(12) United States Patent
Heo et al.

(10) Patent No.: US 12,168,684 B2
(45) Date of Patent: Dec. 17, 2024

(54) ANTIBODY MIMETIC CAPABLE OF BEING ACTIVATED REVERSIBLY AND USES THEREOF

(71) Applicant: INSTITUTE FOR BASIC SCIENCE, Daejeon (KR)

(72) Inventors: Won Do Heo, Daejeon (KR); Yun Ju Lee, Daejeon (KR); Daseuli Yu, Sejong (KR); Byung Ouk Park, Daejeon (KR)

(73) Assignee: INSTITUTE FOR BASIC SCIENCE, Daejeon (KR)

( * ) Notice: Subject to any disclaimer, the term of this patent is extended or adjusted under 35 U.S.C. 154(b) by 280 days.

(21) Appl. No.: 17/468,590

(22) Filed: Sep. 7, 2021

(65) Prior Publication Data

US 2022/0002388 A1 Jan. 6, 2022

Related U.S. Application Data

(62) Division of application No. 15/742,874, filed as application No. PCT/KR2016/015061 on Dec. 21, 2016, now Pat. No. 11,155,604.

(30) Foreign Application Priority Data

Feb. 2, 2016 (KR) .................. 10-2016-0013121

(51) Int. Cl.
C07K 16/00 (2006.01)
C07K 14/00 (2006.01)
C07K 16/14 (2006.01)
C07K 16/18 (2006.01)

(52) U.S. Cl.
CPC .............. *C07K 16/00* (2013.01); *C07K 14/00* (2013.01); *C07K 16/14* (2013.01); *C07K 16/18* (2013.01); *C07K 2317/569* (2013.01); *C07K 2317/622* (2013.01); *C07K 2319/00* (2013.01); *C07K 2319/07* (2013.01); *C07K 2319/60* (2013.01); *C07K 2319/70* (2013.01)

(58) Field of Classification Search
None
See application file for complete search history.

(56) References Cited

U.S. PATENT DOCUMENTS

| 7,166,424 B2* | 1/2007 | Michnick ............. G01N 33/542 530/350 |
| 2010/0183516 A1 | 7/2010 | Ribbert |
| 2012/0165204 A1* | 6/2012 | Hahn .................. C12N 9/16 435/254.11 |

FOREIGN PATENT DOCUMENTS

| KR | 10-2014-0031484 | 3/2014 | |
| WO | WO-2011135040 A1 * | 11/2011 | ........... G01N 33/533 |

OTHER PUBLICATIONS

Lloyd et al. Protein Engineering, Design & Selection 22: 159-168 (Year: 2009).*
Edwards et al., J Mol Biol. 334(1): 103-118 (Year: 2003).*
Rudikoff et al., PNAS 79: 1979-1983 (Year: 1982).*
Kussie et al., J. Immunol. 152: 146-152 (Year: 1994).*
Chen et al., EMBO J., 14: 2784-2794 (Year: 1995).*
Hussain et al., "SNAP-tag technology mediates site specific conjugation of antibody fragments with a photosensitizer and improves target specific phototoxicity in tumor cells", Bioconjugate Chemistry, vol. 22, pp. 2487-2495, 2011.
Kazane et al., "Self-assembled antibody multimers through peptide nucleic acid conjugation", Journal of the American Chemical Society, vol. 135, pp. 340-346, 2013.
Taslimi et al., "An optimized optogenetic clustering tool for probing protein interaction and function", Nature Communications, vol. 5, Article No. 4925, internal pp. 1-9, 2014.
Yuta Nihongaki et al., "Photoactivatable CRISPR-Cas9 for optogenetic genome editing", Nature Biotechnology. 2015, 33(7), 755-760, Jun. 15, 2015.
James S. Huston et al., "Protein engineering of antibody binding sites: Recovery of specific activity in an anti-digoxin single-chain Fv analogue produced in *Escherichia coli*", Proc. Natl. Acad. Soc. USA, 85(16) 5879-5883, Aug. 1988.
M. M. Harmsen et al., "Properties, production, and applications of camelid single-domain antibody fragments", Appl. Microbiol. Biotechnol. 77(1); 13-22, Aug. 18, 2007.
Andrew S. Greenberg et al., "A new antigen receptor gene family that undergoes rearrangement and extensive somatic diversification in sharks", Nature, 374(6518); 168-173, Mar. 9, 1995.
Akiko Koide et al., "The Fibronectin Type III Domain as a Scaffold for Novel Binding Proteins", J. Mol. Biol. 284 (4); 1141-1151, 1998.
Thomas Boehm et al., "VLR-Based Adaptive Immunity", Ann. Rev. Immunol., 30; 203-220, Jan. 3, 2012.
Per-Ake Nygren, "Alternative binding proteins: Affibody binding proteins developed from a small three-helix bundle scaffold", FEBS J., 275(11); 2668-2676, Apr. 24, 2008.
Hilmar Ebersbach et al., "Affilin-Novel Binding Molecules Based on Human γ-B-Crystallin, an All B-Sheet Protein", J. Mol. Biol., 372(1); 172-185, Sep. 7, 2007.
Martin Krehenbrink et al., "Artificial Binding Proteins (Affitins) as Probes for Conformational Changes in Secretin PulD", J. Mol. Biol., 383(5); 1058-1068, Nov. 28, 2008.
Johan Desmet et al., "Structural basis of IL-23 antagonism by an Alphabody protein scaffold", Nat. Commun., 5; 5237, Oct. 30, 2014.
Joshua Silverman et al., "Multivalent avimer proteins evolved by exon shuffling of a family of human receptor domains", Nat. Biotechnol., 23(12); 1556-1561, Apr. 24, 2008.
Michael T. Stumpp et al., "DARPins: A new generation of protein therapeutics", Drug Discov. Today, 13(15-16); 695-701, Aug. 2008.
Dragan Grabulovski et al., "A Novel, Non-immunogenic Fyn SH3-derived Binding Protein with Tumor Vascular Targeting Properties", J. Biol. Chem., 282(5); 3196-3204, Feb. 2, 2007.

(Continued)

Primary Examiner — Phuong Huynh
(74) Attorney, Agent, or Firm — LEX IP MEISTER, PLLC

(57) ABSTRACT

The present invention relates to the preparation of an antibody analogue capable of being activated reversibly, and uses thereof, and provides a fusion protein comprising an inactive first fragment of an antibody analogue is fused to a stimulus-induced dimerization protein.

3 Claims, 11 Drawing Sheets

Specification includes a Sequence Listing.

(56) References Cited

OTHER PUBLICATIONS

Fuun Kawano et al., "Engineered pairs of distinct photoswitches for optogenetic control of cellular proteins", Nature Communication 6:6256, 1-8, Feb. 24, 2015.

Anthony Johnson et al., "Sensitive Affimer and Antibody Based Impedimetric Label-Free Assays for C-Reactive Protein", Anal. Chem. 2012, 84, 6553-6560, Jul. 10, 2012.

Arne Skerra, "Alternative binding proteins: Anticalins—harnessing the structural plasticity of the lipocalin ligand pocket to engineer novel binding activities", FEBS Journal 275(11) 2677-2683, Jun. 2008.

Diana Baumann et al., "A family of GFP-like proteins with different spectral properties in lancelet Branchiostoma floridae", Biology Direct 2008, 3:28, Jul. 3, 2008.

\* cited by examiner

FIG. 2A Tubulin interabody (scFV)
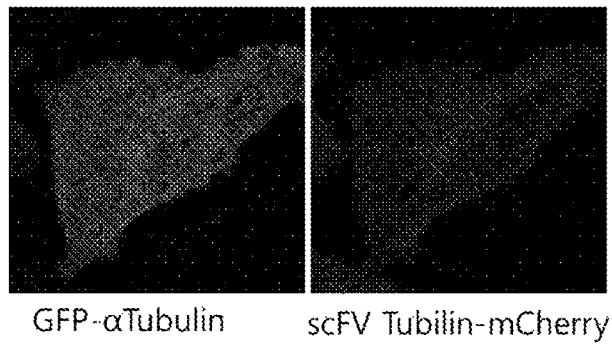
GFP-αTubulin    scFV Tubilin-mCherry
FIG. 2B GFP single domain antibody (nanobody)
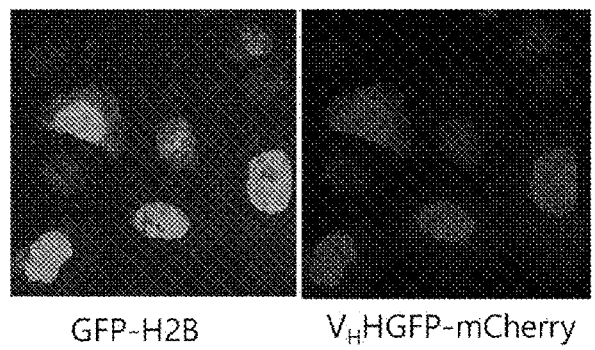
GFP-H2B    V$_H$HGFP-mCherry α-Tubulin interabody (scFV)

Regions in which two antidody fragments are linked artificially

GFP single domain antibody (nanobody)

ANTIBODY MIMETIC CAPABLE OF BEING ACTIVATED REVERSIBLY AND USES THEREOF

This is a divisional application claiming priority to application Ser. No. 15/742,874 filed Jan. 8, 2018 (now U.S. Pat. No. 11,155,604), which is a 35 U.S.C. § 371 National Phase Entry application from PCT/KR2016/015061 filed on Dec. 21, 2016, and designating the United States, which claims priority under 35 U.S.C. § 119 to Korean Patent Application No. 10-2016-0013121 filed on Feb. 2, 2016, the entire disclosures of which are incorporated herein by reference.

TECHNICAL FIELD

The present invention relates to an antibody analogue and uses thereof, and more specifically, to an antibody analogue capable of being activated reversibly, and uses thereof.

BACKGROUND ART

Antibodies are major indicators used for studying intracellular signaling processes. In particular, fluorescently-labeled antibodies are critical markers used in molecular imaging techniques to identify the results of molecular interactions with antigens of interest in cells. Accordingly, conventional full-length antibodies are widely used in the fields of applied biochemistry and cell biology, as well as for therapeutic purposes. However, full-length antibodies are basically heterotetramers produced by combining two strands of heavy chains and two strands of light chains, and it has been reported that functional antibodies are not well-produced by a recombinant method in mammals. This characteristic is a factor that greatly limits the ability to study the functions of an intracellular protein by expressing the full-length antibody of the protein in a cell via a recombinant method, or the ability to use the intracellular protein to treat associated diseases by controlling the functions thereof. As an alternative, it is possible to conceive of a technique of delivering a full-length antibody into a cell in a protein state, but protein delivery techniques for antibodies yet to be satisfactorily commercialized.

As an alternative method to the full-length antibody, antibody analogues which have a smaller size and retain antigen-binding capacity have been developed. Representative examples of these antibody analogues include: a single chain variable fragment (hereinafter abbreviated as "scFv", Huston et al., *Proc. Natl. Acad. Sci. USA*, 85(16): 5879-5883, 1988), a camelid-derived single-domain antibody fragment known as Nanobody (hereinafter abbreviated as "$V_HH$", Harmsem and Haard, *Appl. Microbiol. Biotechnol.* 77(1): 13-22, 2007), a variable new antigen receptor derived from Chondrichthyes such as sharks (hereinafter abbreviated as "$V_{NAR}$", Greenberg et al., *Nature*, 374(6518): 168-173, 1995), a monobody, which is a synthetic binding protein derived from fibronectin type 3 domain (FN3) (Koide et al., *J. Mol. Biol.* 284 (4): 1141-1151, 1998), a variable lymphocyte receptor derived from jawless vertebrates such as arctic lamprey and inshore hagfish (hereinafter, "VLR", Boehm et al., *Ann. Rev. Immunol.*, 30: 203-220, 2012), Affibody derived from Z domain of protein A (Nygren, *FEBS J.*, 275(11): 2668-2676, 2008), Affilin derived from human gamma-B-crystalline (Ebersbach et al., *J. Mol. Biol.*, 372(1): 172-185, 2007), Affimer derived from cystatin (Johnson et al., *Anal. Chem.*, 2012), Affitin derived from *Sulfolobus acidocaldarius* Sac7d (Krenhenbrink et al., *J. Mol. Biol.*, 383(5): 1058-1068, 2008), Alphabody derived from triple helix coiled coil protein (Desmet et al., *Nat. Commun.*, 5: 5237, 2014), Anticlin derived from lipocalin (Skerra A., *FEBS J.*, 275(11): 2677-2083, 2008), Avimer which is one of the domains of versatile membrane receptors (Silverman et al., *Nat. Biotechnol.*, 23(12): 1556-1561, 2005), DARpin derived from ankyrin repeat motif (Stumpp et al., *Drug Discov. Today*, 13(15-16): 695-701, 2008), Fynomer derived from the SH3 domain of Fyn protein (Grabulovski et al., *J. Biol. Chem.*, 282(5): 3196-3204, 2007), Kunitz domain peptide derived from the Kunitz domain of various protease inhibitors (Nixon et al., *Curr. Opin. Drug Discov. Devel.*, 9(2): 261-268, 2006), etc. All of these antibody mimics are single-stranded and have a size of about 5 kDa to 20 kDa, and can be expressed in cells by transcription and translation upon introduction of a gene into cells by a recombinant method, or can be introduced into cells in a protein state using a conventional carrier for intracellular delivery of proteins.

DISCLOSURE OF THE INVENTION

Technical Problem

However, these antibody analogues have a disadvantage in that it is difficult to appropriately study the intracellular distribution or functions of target antigen proteins because the intracellular delivery efficiency of these antibody analogues is not high, and also in that, when these antibody analogues are expressed in cells in a recombinant manner, the antibody analogues interact with target antigen proteins present in the cells from the moment the antibody analogues are expressed.

The present invention, which is intended to solve various problems including the above problems, aims to provide an antibody analogue which can be used not only in vitro but also in vivo, and can be reversibly activated by a particular stimulus, and to provide a use thereof.

However, these objects are merely exemplary, and the scope of the present invention should not be limited thereto.

Technical Solution

An aspect of the present invention provides a fusion protein comprising an inactive first fragment of an antibody analogue is fused to a stimulus-induced dimerization protein.

Another aspect of the present invention provides a fusion protein comprising an inactive second fragment of an antibody analogue is fused to a stimulus-induced dimerization partner protein which forms a dimer with a stimulus-induced dimerization protein upon stimulation, wherein the inactive second fragment recovers antigen-binding capacity when bound to the inactive first fragment by dimerizing of the stimulus-induced dimerization protein and the stimulus-induced dimerization partner protein induced by the stimulus.

Still another aspect of the present invention provides a polynucleotide which encodes the fusion protein.

Still another aspect of the present invention provides a recombinant vector including the polynucleotide.

Still another aspect of the present invention provides a composition which including the fusion protein.

Still another aspect of the present invention provides a pharmaceutical composition comprising the recombinant vector as an active ingredient and is used for the treatment of diseases that occur due to the overexpression of an antigen.

Still another aspect of the present invention provides a method for activating the antibody analogue, the method including: introducing a first fusion protein comprising an inactive first fragment of an antibody analogue is fused to a stimulus-induced dimerization protein, and a second fusion protein comprising an inactive second fragment of an antibody analogue is fused to a stimulus-induced dimerization partner protein which forms a dimer with the stimulus-induced dimerization protein upon stimulation, wherein the inactive second fragment recovers antigen-binding capacity when bound to the inactive first fragment by dimerizing of the stimulus-induced dimerization protein and the stimulus-induced dimerization partner protein induced by a stimulus to a subject, tissue, or cell; and applying the stimulus to the subject, tissue or cell, wherein the stimulus induces dimerization of the stimulus-induced dimerization protein and the stimulus-induced dimerization partner protein.

Still another aspect of the present invention provides a method for activating the antibody analogue, the method including: transducing a subject, tissue or cell with a first polynucleotide encoding a first fusion protein comprising an inactive first fragment of an antibody analogue is fused to a stimulus-induced dimerization protein, and a second polynucleotide encoding a second fusion protein comprising an inactive second fragment of an antibody analogue is fused to a stimulus-induced dimerization partner protein which forms a dimer with the stimulus-induced dimerization protein upon stimulation, wherein the inactive second fragment recovers antigen-binding capacity when bound to the inactive first fragment by dimerizing of the stimulus-induced dimerization protein and the stimulus-induced dimerization partner protein induced by a stimulus; and applying the stimulus to the subject, tissue or cell, wherein the stimulus induces dimerization of the stimulus-induced dimerization protein and the stimulus-induced dimerization partner protein.

Advantageous Effects

According to an embodiment of the present invention as described above, an antibody analogue can be activated by light and reversibly regulated in an animal or plant cell. Obviously, the scope of the present invention is not limited thereto.

BRIEF DESCRIPTION OF THE DRAWINGS

FIGS. 2A and 2B show fluorescence microscopy images confirming that scFv and nanobody expressed in cells bind to each antigen.
FIG. 2A shows fluorescence microscopy images of cells in which a fusion protein of GFP-αTubulin (left) and a fusion protein of anti-tubulin αTubulin intrabody (scFv)-mCherry (right) were co-expressed,
and FIG. 2B shows fluorescence microscopy images of cells in which a fusion protein of GFP-histone 2B (H2B) (left) and a fusion protein of anti-GFP nanobody($V_HH$)-mCherry (right) were co-expressed.

FIG. 4A is a schematic diagram illustrating linker portions artificially connecting two antibody fragments ($V_H$ and $V_L$) by the structure of αtubulin intrabody and potential split positions thereof,
and FIG. 4B is a schematic diagram illustrating the structure and sequences of a GFP single-domain antibody (nanobody) having complementarity-determining groups CDR1, CDR2, and CDR3, in which the inverted triangles represent potential split regions.
  CDR: complementarity-determining regions
  GFP: green fluorescence protein
  Lamin: intermediate filament; Fibrous protein
  Actin: microfilament; spherical multi-functional protein
FIG. 7A shows fluorescence microscopy images of a control group of HeLa cells in which the mCherry-$V_H$HGFP construct and the GFP-H2B construct are co-transfected (left), and fluorescence microscopy images of HeLa cells in which the split N-term $V_H$HGFP-nMagH-mCherry construct (a first fragment) and the iRFP-pMagH-C-term $V_H$HGF construct (a second fragment) of the present invention are co-transfected together with the GFP-H2B construct, before and after light irradiation (right).
FIG. 7B is a graph showing the fluorescence intensity ratio between nuclei and cytoplasm in a series of fluorescence microscopy images according to time after light irradiation.
FIG. 8A shows fluorescence microscopy images of a control group of HeLa cells in which the mCherry-$V_H$HGFP construct and the TOMM20-EGFP construct are co-transfected (left), and fluorescence microscopy images of HeLa cells in which the split N-term $V_H$HGFP-nMagH-mCherry construct (a first fragment) and the iRFP-pMagH-C-term $V_H$HGF construct (a second fragment) of the present invention are co-transfected together with the TOMM20-EGFP construct, before and after light irradiation (right).
FIG. 8B is a graph showing the Pearson correlation coefficient of red fluorescence to EGFP signal (green fluorescence) at the same position in a series of fluorescence microscopy images according to time after light irradiation.
FIG. 9A shows fluorescence microscopy images of a control group of HeLa cells in which the scFvGCN4-FuRed construct and the Mito-GFP-24XGCN4pep construct are co-transfected (left), and fluorescence microscopy images of HeLa cells in which the split N-term scFvGCN4-nMagH-FuRed construct (a first fragment) and the iRFP-pMagH-C-term scFvGCN4 construct of the present invention are co-transfected together with the Mito-GFP-24XGCN4pep construct, before and after light irradiation (right).
FIG. 9B is a graph showing the Pearson correlation coefficient of red fluorescence to EGFP signal (green fluorescence) at the same position in a series of fluorescence microscopy images according to time after light irradiation.

FIG. 10A shows fluorescence microscopy images of a control group of HeLa cells in which the mCherry-$V_H$HGFP construct and the Mito-TOMM20-EGFP construct are co-transfected (left), and fluorescence microscopy images of HeLa cells in which the N-term $V_H$HGFP-FRB-FuRed-P2A-FKBP-C-term $V_H$HGF construct encoding the split fusion proteins of the present invention is co-transfected together with the TOMM20-EGFP construct, before and after light irradiation (right). FIG. 10B is a graph showing the Pearson correlation coefficient of red fluorescence to EGFP signal (green fluorescence) at the same position in a series of fluorescence microscopy images according to time after rapamycin treatment.

BEST MODE FOR CARRYING OUT THE INVENTION

Figure 1:
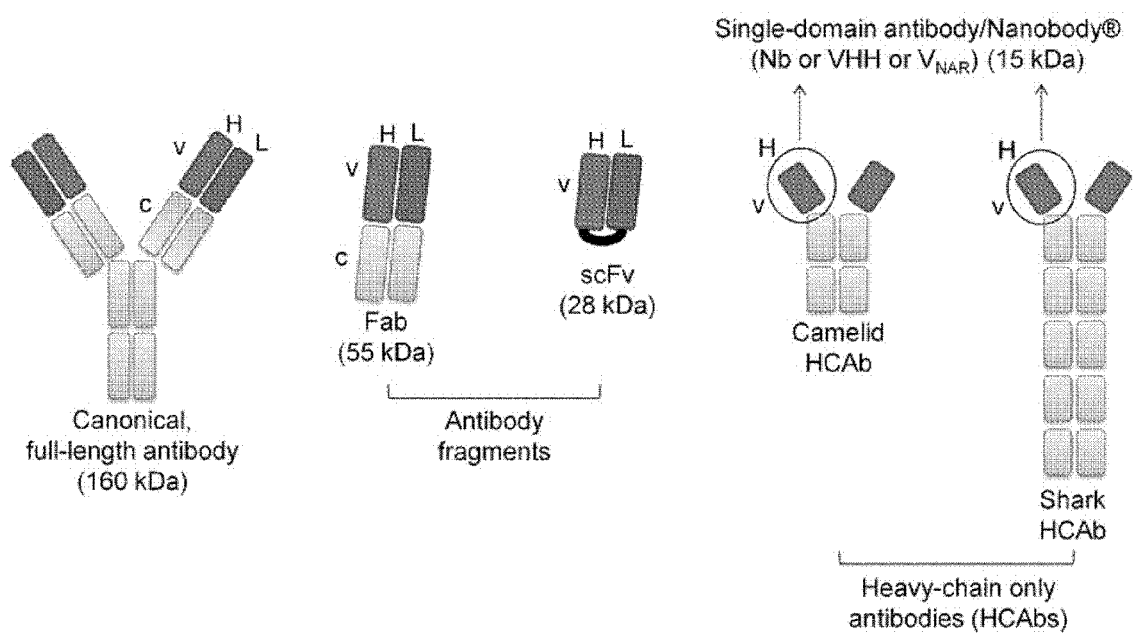
FIG. 1 is a schematic diagram illustrating the structure of a typical antibody and a part thereof that can be used as an antibody.
  HCAbs: Heavy-chain antibodies;
  $V_HH$: Variable domain of heavy-chain camelid antibody (Nanobody);
  Fab: fragment-antigen binding;
  Fc: fragment crystalline;
  scFv: single-chain variable fragment;
  $V_H$: variable domain of the heavy chain;
  $V_L$: variable domain of the light chain.
Figure 3:
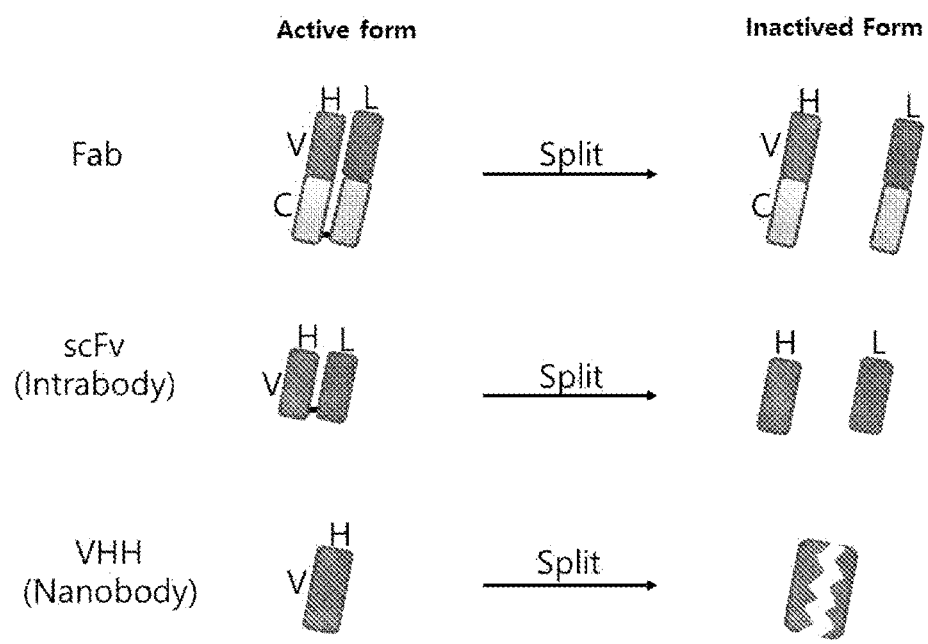
FIG. 3 is a schematic diagram illustrating the induction of inactivation of antibody fragments via protein splitting.
Figure 4A:
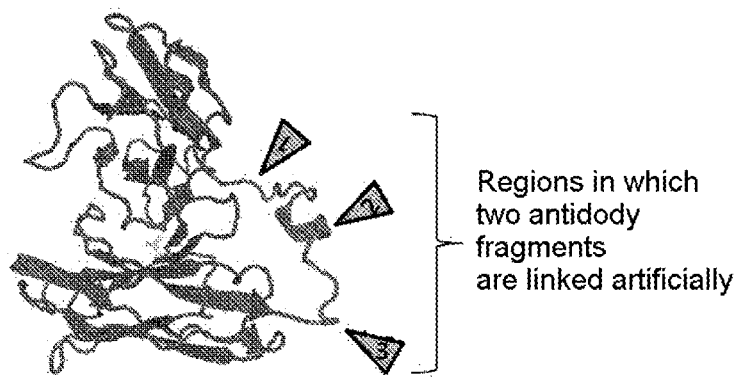
FIGS. 4A and 4B show protein splitting positions for inducing inactivation of antibody fragments.
Figure 4B:
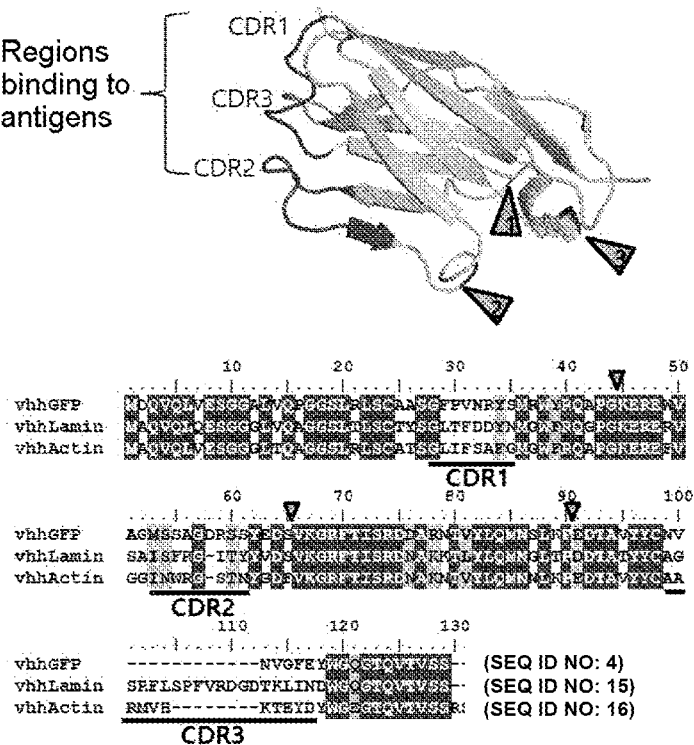
Figure 5:
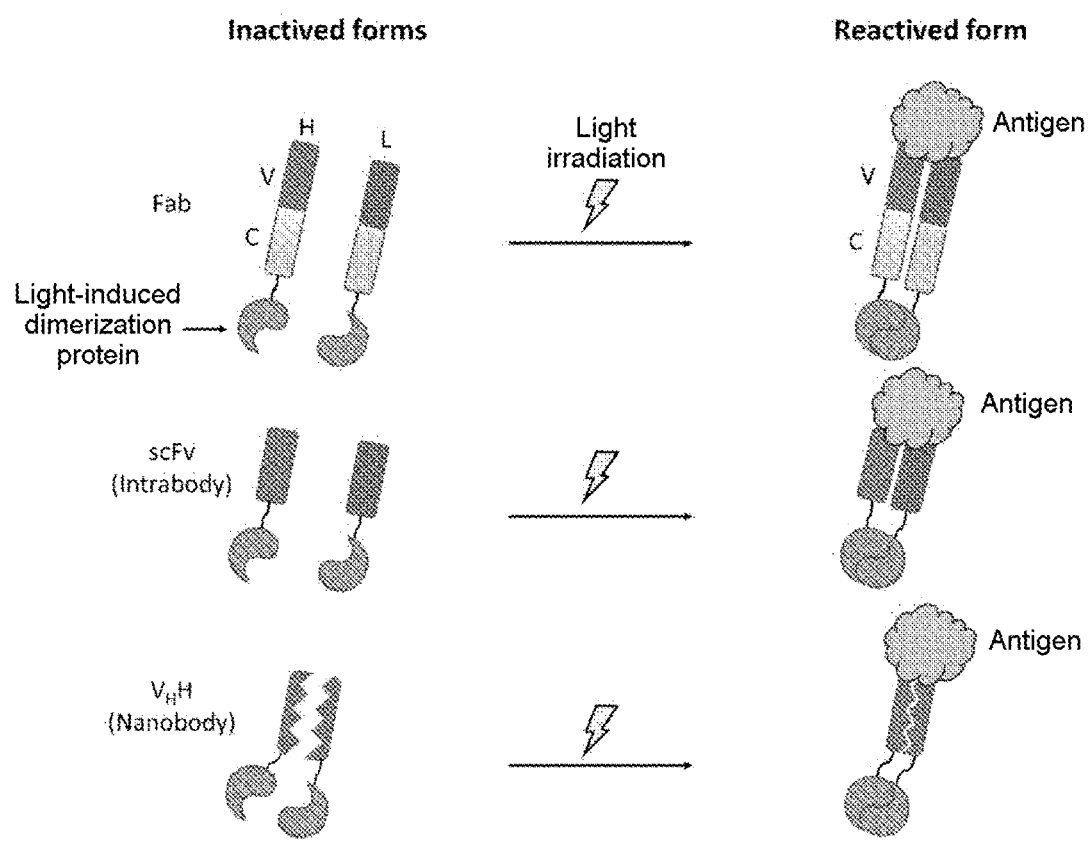
FIG. 5 is a schematic diagram illustrating a light-induced activation process of inactivated antibody fragments by protein splitting.
Figure 6:
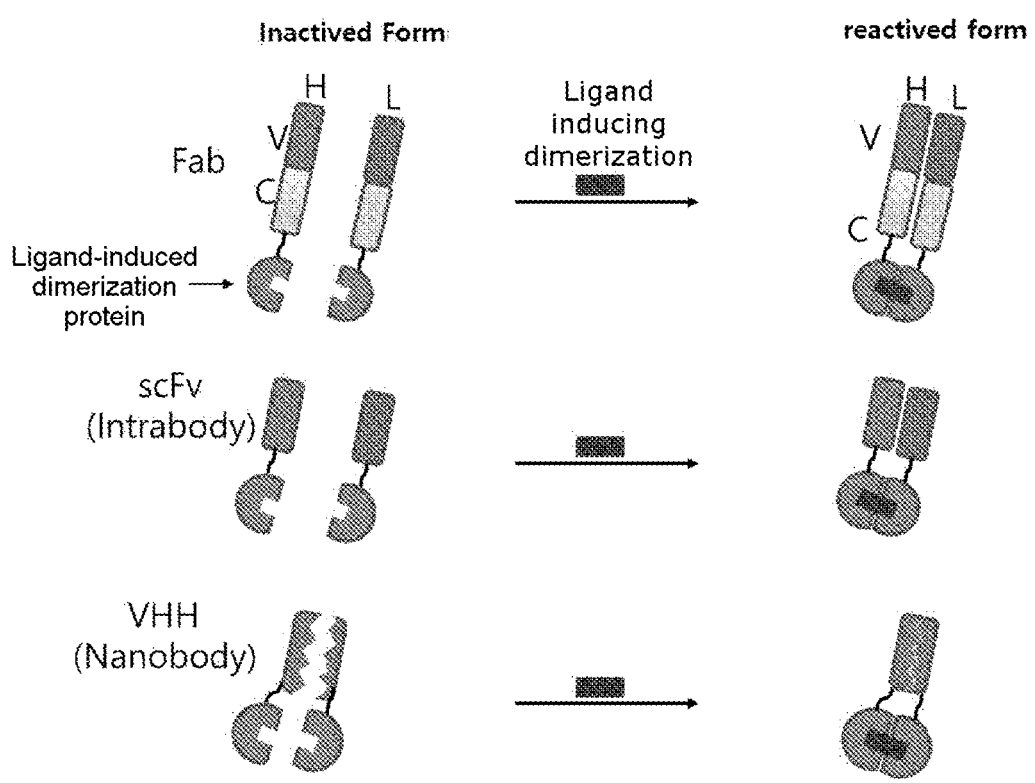
FIG. 6 is a schematic diagram illustrating a ligand-induced activation process of inactivated antibody fragments by protein splitting.

The terms used in the present invention are defined as follows.

As used herein, the term "antibody analogue" or "antibody mimetic", is a concept which includes fragments that include the smallest units maintaining antigen-binding capacity (e.g., Fab, F(ab')$_2$, Fab' or a single-chain variable fragment (scFv)) which is an artificial fragment linked to a variable region of a heavy chain and a light chain or antibody fragments from camelids or Chondrichthyes ($V_HH$, $V_{NAR}$, etc.) consisting of only heavy chains without light chains, and antibody mimetic proteins prepared from a non-antibody-derived protein scaffold, such as a nanobody, monobody, or variable lymphocyte receptor (VLR), unlike conventional full-length antibodies consisting of two heavy chains and two light chains which form a quaternary heterotetramer structure for the function.

As used herein, the term "monobody" is a synthetic binding protein constructed using the fibronectin type III domain (FN3) as a molecular scaffold. Monobody was first introduced by the Koide research group in 1998 as a simple yet robust alternative to antibodies as target-binding proteins (Koide et al. *J. Mol. Biol.* 284: 1141-1151, 1998).

As used herein, the term "nanobody", so named by the developer Ablynx, is an antibody fragment consisting of a single monomer variable antibody domain derived from the heavy chain of a camelid antibody, and is also known as a $V_H$H fragment. Unlike conventional mammalian antibodies consisting of two strands each of a heavy chain and a light chain, the camelid antibody is a unique antibody consisting of only two heavy chains (Harmsen et al., *Appl. Microbiol. Biotechnol.* 77(1): 13-22, 2007). The nanobody can selectively bind to a specific antigen, like conventional mammalian antibodies, and has a molecular weight of only 12 kDa to 15 kDa, which is less than one tenth of the size of conventional antibodies (150 kDa to 160 kDa). In addition to $V_H$H, fragments derived from the light chain variable region or the heavy chain variable region of a conventional antibody can also be selectively bound to a particular antigen by replacing a lipophilic amino acid with a hydrophilic one, but this is not always successful. Furthermore, in addition to the camelid-derived monovalent antibody, a variable region of IgNAR, which is a monovalent antibody derived from sharks, may be used as a single-chain variable fragment.

As used herein, the term "VLR" is an abbreviation for variable lymphocyte receptor which, as a molecule regulating the acquired immune response in jawless vertebrates (e.g., arctic lamprey and inshore hagfish), is a receptor belonging to the single-chain leucine-rich repeating unit family unlike conventional antibodies, but has a specific binding ability to a particular antigen (Boehm et al., *Ann. Rev. Immunol.* 30: 203-220, 2012). RepeBody (Lee et al., *Mol. Ther.* 22(7): 1254-1265, 2014), which is a recombinant protein prepared by random mutagenesis of VLRs to increase affinity for a specific protein, may also be regarded as belonging to the VLR.

As used herein, the term "Affybody", which refers to a small (6 kDa) protein that can specifically bind to a particular antigen wherein the Affibody is based on a small, robust protein scaffold, Z domain of protein A, consists of three alpha helices and does not have a disulfide bond (Nygren, P. A., *FEBS J.* 275(11): 2668-2676, 2008).

As used herein, the term "Affilin", which refers to an artificial peptide capable of selectively binding to a specific antigen, is a registered trademark of Scil Proteins GmbH. Affilin is derived from human ubiquitin protein or gamma-B crystalline, which is a scaffold. Affilin can be selected using a screening technique, such as phage display, after modification of surface-exposed amino acids of the proteins (Ebersbach et al., *J. Mol. Biol.* 372(1): 172-185, 2008).

As used herein, the term "Affimer" refers to a single-chain-based antibody analogue capable of specifically binding to a particular antigen which is derived from a cystatin-based cysteine protease inhibitor, which is a scaffold. Affimer was first developed at the MRC Cancer Cell Unit in Cambridge (Johnson et al., Anal. Chem. 84(15): 6553-6560, 2012).

As used herein, the term "Affitin" refers to a scaffold protein which is a single chain-based antibody mimetic derived from Sac7d (i.e., a DNA binding protein). Affitin can selectively bind to a specific antigen and has a molecular weight of about 7 kDa (Krehenbrink et al., *J. Mol. Biol.,* 383(5): 1058-1068, 2008).

As used herein, the term "Alphabody" refers to a small single chain-based antibody analogue of about 10 kDa, and is also called a cell-penetrating alphabody. Alphabody is not derived from a native scaffold protein but is a single-chain protein with an alpha-helical structure designed through computer modeling and inspired by a coiled-coil protein structure, and was developed by Belgian biotechnology company Compix N.V (Desmet et al., *Nature Communications,* 5: 5237, 2014).

As used herein, the term "Anticalin" refers to a scaffold protein which is a single-chain-based antibody analogue capable of specifically binding to a specific antigen derived from human lipocalin, and which has a size of about 20 kDa and consists of about 180 amino acids. Anticalin was developed by Pieris Pharmaceuticals, Inc. of Germany (Skerra A., *FEBS J.,* 275(11): 2677-2683, 2008).

As used herein, the term "Avimer" refers to a single chain-based antibody mimetic, in which two or more peptides consisting of 30-35 amino acids derived from the A domain of various membrane receptors are linked by a linker peptide, and has selective binding ability to specific antigens. Avimer was developed by Avidia, a subsidiary of Amgen Inc. (Silverman et al. *Nat. Biotechnol.* 23(12): 1556-1561, 2005).

As used herein, the term "DARpin", an abbreviation for "designed ankyrin repeat protein", refers to an antibody mimetic protein having high selectivity and high affinity for a specific heterologous protein derived from ankyrin as can be inferred from the name. DARpin has a molecular weight of 14 kDa or 18 kDa, consists of 4 or 5 repeats of DARpin, and was developed by Molecular Partners AG of Germany (Stumpp et al., *Drug Discov. Today*, 13(15-16): 695-701, 2008).

As used herein, the term "Fynomer" refers to an antibody mimetic which has a molecular weight of about 7 kDa and is derived from the $SH_3$ domain of the Fyn protein as a scaffold protein (Grabulosyski et al., *J. Biol. Chem.*, 282(5): 3196-3204, 2006).

As used herein, the term "Kunitz domain" refers to an active domain of a protein inhibiting the function of a protease, and is a single chain-based peptide having a size of about 6 kDa and consisting of 50 to 60 amino acids. The Kunitz domain is a peptide that serves as a competitive protease inhibitor and can be screened through techniques such as phage display from libraries containing more than 10 million variants (Nixon and Wood, *Curr. Opin. Drug Discov. Devel.* 9(2): 261-268, 2006).

As used herein, the term "inactivated fragment of an antibody analogue" refers to a protein fragment produced by splitting the functional minimal unit protein of the antibody analogue at an appropriate position. The inactivated fragment of the antibody analogue, when expressed alone and when co-expressed with the opposing inactivated fragment, does not have the structure and function of an antibody analogue and thus has no antigen-binding capacity. As such, the fragment is referred to as an "inactive fragment", and as used herein, the two fragments produced by splitting are referred to as a first fragment and a second fragment for convenience. The N-terminal fragment and the C-terminal fragment may both be referred to as the first fragment. However, when the antibody analogue is Fab, the first and second fragments may be a heavy chain variable domain and a light chain variable domain, or a light chain variable domain and a heavy chain variable domain, respectively.

As used herein, the term "stimulus-induced dimerization protein" refers to a protein that forms a homodimer or forms a heterodimer with a partner protein when a particular stimulus is applied thereon. Among these stimulus-induced dimerization proteins, a light-induced dimerization protein which forms a dimer upon irradiation of light with a specific wavelength, and a ligand-induced dimerization protein which forms a dimer upon treatment with a particular compound are present. In addition, although not yet elucidated, it is presumed that there are some proteins that form dimers when subjected to ultrasonic, magnetic, or heat treatment.

As used herein, the term "light-induced dimerization protein" refers to a protein that forms a homodimer or forms a heterodimer with a partner protein when light with a particular wavelength is irradiated thereon.

As used herein, the term "ligand-induced dimerization protein" refers to a protein that forms a homodimer or forms a heterodimer with a partner protein when treated with a particular compound.

As used herein, the term "heterodimer" refers to a single complex which is formed by the interaction between two different proteins.

As used herein, the term "homodimer" refers to a single complex which is formed by the interaction between two identical proteins.

As used herein, the term "partner protein" refers to a subject protein that forms a homodimer or heterodimer by interacting with a stimulus-induced dimerization protein upon applying a stimulus.

As used herein, the term "PHR" indicating the N-terminal region of the CRY refers to a photolyase homology region, which interacts with the CIB or CIBN upon light irradiation (Kennedy et al., *Nat. Methods*, 7(12): 973-975, 2010).

As used herein, the term "CIB" refers to a cryptochrome-interacting basic-helix-loop-helix protein, and a representative example is the CIB1 of *Arabidopsis thaliana* (GenBank No.: NM_119618).

As used herein, the term "CIBN", indicating the N-terminal region of the CIB, refers to a region that interacts with cryptochrome (CRY) upon light irradiation.

As used herein, the term "CRY" refers to a chryptochrome protein, and a representative example is the CRY2 of *Arabidopsis thaliana* (GenBank No.: NM_100320).

As used herein, the term "PHR'", indicating the N-terminal region of the CRY, refers to a phytolyase homologous region that interacts with the CIB or CIBN upon light irradiation (Kennedy et al., *Nat. Methods*, 7(12): 973-975, 2010).

As used herein, the term "Phy" refers to a phytochrome protein, and representative examples include PhyA (GenBank No.: NM_001123784) and PhyB (GenBank No.: NM_127435) of *Arabidopsis thaliana*. Phy is known to interact with a phytochrome interacting factor (PIF) (Min et al., *Nature*, 400: 781-784, 1999).

As used herein, the term "PIF" refers to a phytochrome interacting factor, and representative examples include PIF1 (GenBank No.: NM_001202630), PIF3 (GenBank No.: NM_179295), PIF4 (GenBank No.: NM_180050), PIFS (GenBank No.: NM_180690), PIF6 (GenBank No.: NM_001203231), and PIF7 (GenBank No.: NM_125520) of *Arabidopsis thaliana*.

As used herein, the term "FKF" refers to a Flavin-binding, Kelch repeat, F-box protein, and a representative example is the FKF1 of *Arabidopsis thaliana* (GenBank No.: NM_105475). KFK is known to interact with the GIGANTEA protein upon light irradiation (Sawa et al., *Science*, 318(5848): 261-265, 2007).

As used herein, the term "GIGANTEA" is associated with a phytochrome signaling pathway and is known as a protein controlling the flowering time of flowers.

As used herein, the term "tetracysteine motif" refers to a polypeptide which includes the sequence of Cys-Cys-Xaa-Xaa-Cys-Cys (SEQ ID NO: 1), where Xaa is an amino acid excluding cysteine. The fluorescence pattern varies depending on the type of Xaa and the length of the polypeptide (Adams et al., *J. Am. Chem. Soc.*, 124: 6063-6077, 2002).

As used herein, the term "nMag" refers to a variant of the Vivid protein system and is an abbreviation for negative Magnet, which is known to form a heterodimer upon irradiation of Positive Magnet (pMag) and 488 nm-light, and can be classified into three types (i.e., nMagFast1, nMagFast2, and nMagHigh1) according to the type of variation (Kawano et al., *Nat. Comm.*, 6: 6256, 2015).

As used herein, the term "pMag" refers to a variant of the Vivid protein system and is an abbreviation for positive Magnet, which is known to form a heterodimer upon irradiation of the nMag and 488 nm-light, and like the nMag, can be classified into three types (i.e., pMagFast1, pMagFast2, and pMagHigh1) (Kawano et al., *Nat. Comm.*, 6: 6256, 2015).

As used herein, the term "FK506 Binding Protein (FKBP)" refers to a protein which is associated with cyclophilin in terms of function, has prolyl isomerase activity, and is known to function as a protein folding chaperone of proteins with a proline residue. FK506 Binding Protein is also known to interact with FKBP, Calcineurin A, CyP-Fas, and FRB upon treatment of the particular compounds FK1012, FK506, FKScA, and rapamycin, respectively, to thereby form a dimer.

As used herein, the term "Calcineurin A" refers to the calcium and calmodulin-dependent serine/threonine protein dephosphorylases, and is known to form a heterodimer with FKBP when treated with compound FK506.

As used herein, the term "Cyp-Fas" refers to a kind of chimeric protein in which CyP (cyclophillin) protein and Fas receptor protein are linked, and is known to form a heterodimer with FKBP when treated with AFKCsA, which is a compound synthesis cyclosporin A (Belshaw et al., *Proc. Natl. Acad. Soc. U.S.A.,* 93: 4604-4607, 1996).

As used herein, the term "FKBP-rapamycin-binding protein (FRB)" refers to a domain that binds to FKBP and rapamycin in the mTOR protein, and is known to interact with FKBP to form a heterodimer when treated with rapamycin (Rivera et al., *Nat. Med.,* 2(9): 1028-1032, 1996).

As used herein, the term "GyrB" refers to a DNA gyrase subunit B, which plays a role in eliminating DNA supercoils by cutting ATP-dependent double-stranded DNA in an ATP-dependent manner, and then passing through and recombining the ATP-dependent double-stranded DNA. GyrB is known to form a heterodimer when treated with antibiotics (Farrar et al., *Nature,* 383(6596): 178-181, 1996).

As used herein, the term "gibberellin insensitive (GAI)" refers to a protein involved in the responsiveness of gibberellin, a plant hormone, and is known to form a heterodimer with gibberellin insensitive dwarf 1 (GID1) when treated with gibberellin (Wilson and Somerville, *Plant Physiol.,* 108: 495-502, 1995).

As used herein, the term "gibberellin insensitive dwarf 1 (GID1)" refers to a protein involved in the responsiveness of gibberellin, a plant hormone, and is known to form a heterodimer with gibberellin insensitive (GAI) when treated with gibberellin (Wilson and Somerville, *Plant Physiol.,* 108: 495-502, 1995).

As used herein, the term "Snap-tag" refers to an improved protein of O-6-methylguanine-DNA methyltransferase, and is a 19.4 kD protein consisting of 182 amino acids. SNAP-tag is known to form a heterodimer with Halo-tag when treated with HaXS, which is a fluorescent compound (Erhart et al., *Chem. Biol.,* 20(4): 549-557, 2013).

As used herein, the term "Halo-tag" refers to a synthetic ligand that was originally developed as a tag for the purification of proteins, and is known to form a heterodimer with the Snap-tag when treated with HaXS, which is a fluorescent compound (Erhart et al., *Chem. Biol.,* 20(4): 549-557, 2013).

As used herein, the term "operably linked to" indicates that a particular polynucleotide is linked to another polynucleotide to carry out the function of the other polynucleotide. That is, the fact that a polynucleotide encoding a particular protein is operably linked to a promoter means that the polynucleotide is ligated to be transcribed into mRNA by the action of the corresponding promoter and ultimately translated into the corresponding protein, and the fact that a polynucleotide encoding a specific protein is operably linked to a polynucleotide encoding another protein means that the corresponding particular protein is linked to be expressed in the form of a fusion protein with another protein.

Hereinafter, the present invention is explained in detail.

In accordance with an aspect of the present disclosure, the provided is a fusion protein comprising an inactive first fragment of an antibody analogue is fused to a stimulus-induced dimerization protein.

In accordance with another aspect of the present disclosure, the provided is a fusion protein comprising an inactive second fragment of an antibody analogue is fused to a stimulus-induced dimerization partner protein which forms a dimer with a stimulus-induced dimerization protein upon stimulation, wherein the inactive second fragment recovers antigen-binding capacity when bound to the inactive first fragment by dimerizing of the stimulus-induced dimerization protein and the stimulus-induced dimerization partner protein induced by the stimulus.

In the fusion protein, the first and second fragments are fragments generated by cleaving the antibody analogue at appropriate positions, in which the appropriate positions exclude the CDR, and may be an intermolecular disulfide bond, linker region, non-CDR loop region, or hinge region of the antibody analogue.

In the fusion protein, the antibody analogue is Fab, F(ab')$_2$, Fab', V$_H$H, monobody, VLR, repebody, Affibody, Affilin, Affimer, Affitin, Alphabody, Anticalin, Avimer, DARpin, Fynomer, or Kunitz domain peptide.

The fusion protein may further include a fluorescent protein.

In particular, the fusion protein may be a green fluorescent protein (GFP), yellow fluorescent protein (YFP), red fluorescent protein (RFP), orange fluorescent protein (OFP), cyan fluorescent protein (CFP), blue fluorescent protein (BFP), far-red fluorescent protein, or tetracystein motif. In particular, the green fluorescent protein may be enhanced green fluorescent protein (EGFP), Emerald, Superfolder, GFP, Azami Green, TagGFP, TurboGFP, ZsGreen, or T-Sapphire; the yellow fluorescent protein may be enhanced yellow fluorescent protein (EYFP), Topaz, Venus, mCitrine, Ypet, TagYFP, PhiYFP, ZsYellow1, or mBanana; the red fluorescent protein may be mRuby, mApple, mStrawberry, AsRed2, or mRFP; the orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer, or mTangerine; the cyan fluorescent protein may be enhanced cyan fluorescent protein (ECFP), mECFP, mCerulean, CyPet, AmCyan1, Midori-Ishi Cyan, TagCFP, or mTFP1; the blue fluorescent protein may be enhanced blue fluorescent protein (EBFP), EBFP2, Azurite, or mTagBFP; the far-red fluorescent protein may be mPlum, mCherry, dKeima-Tandem, JRed, mRaspberry, HcRed1, HcRed-Tandem, or AQ143; and the tetracysteine motif may be a polypeptide including the sequence Cys-Cys-Xaa-Xaa-Cys-Cys (SEQ ID NO: 1), in which the Xaa may be an amino acid excluding cysteine.

The stimulus may be a ligand or light, the stimulus-induced dimerization protein is a ligand-induced dimerization protein when the above stimulus is a ligand and a protein which forms a dimer with the ligand-induced dimerization protein is a ligand-induced dimerization partner protein, and the stimulus-induced dimerization protein is a light-induced dimerization protein when the stimulus is light and a protein which forms a dimer with the light-induced dimerization protein is a light-induced dimerization partner protein.

The ligand-induced dimerization protein may be FK506 binding protein (FKBP), Calcineurin A, Cyp-Fas, FKBPrapamycin-binding protein (FRB), GyrB, GAI (gibberellin insensitive), gibberellin insensitive dwarf 1 (GID1), Snap-tag, or Halo-tag.

The ligand-induced dimerization partner protein may be FKBP, Calcineurine, Cyp-Fas, or FRB when the ligand-induced dimerization protein is FKBP; the ligand-induced dimerization partner protein may be FKBP when the ligand-induced dimerization protein is Calcineurin A, Cyp-Fas, or FRB; the ligand-induced dimerization partner protein may be GyrB when the ligand-induced dimerization protein is GyrB; the ligand-induced dimerization partner protein may be GID1 when the ligand-induced dimerization protein is GAI, whereas the ligand-induced dimerization partner protein may be GAI when the ligand-induced dimerization protein is GID1; and the ligand-induced dimerization partner protein may be Halo-tag when the ligand-induced dimerization protein is Snap-tag, whereas, the ligand-induced dimerization partner protein may be Snap-tag when the ligand-induced dimerization protein is Halo-Tag.

In the above case, the ligand which induces a homodimer between FKBP and FKBP is FK1012; the ligand which induces a heterodimer between FKBP and Calcineurin A is FK506; the ligand which induces a heterodimer between FKBP and Cyp-Fas is FKCsA; the ligand which induces a heterodimer between FKBP and FRB is rapamycin; the ligand which induces a homodimer between GyrB and CyrB is coumermycin; the ligand which induces a heterodimer between GAI and GID1 is gibberellin; and the ligand which induces a heterodimer between Snap-tag and Halo-tag is HaXS.

The light-induced dimerization protein may be a light-induced heterodimerization protein and/or light-induced homodimerization protein. The light-induced heterodimerization protein may be cryptochrome-interacting basic-helix-loop-helix protein (CIB), N-terminal domain of CIB (CIBN), phytochrome (Phy), phytochrome interacting factor (PIF), Flavin-binding, Kelch repeat, F-box 1 (FKF1), GIGANTEA, chryptochrome (CRY), phytolyase homologous region (PHR), nMag, or pMag; and the light-induced homodimerization protein may be CRY or PHR. Conventionally, CRY or PHR is known to form homodimers irrespective of light irradiation, but the present inventors have discovered that CRY or PHR forms a homodimer by light irradiation. Therefore, CRY or PHR is a protein which not only forms heterodimers by light irradiation, but also forms homodimers by light irradiation.

In the above fusion protein, the light-induced dimerization protein may be a light-induced heterodimerization protein or light-induced homodimerization protein, and the light-induced heterodimerization protein may be CIB, CIBN, PhyB, PIF, FKF1, GIGANTEA, CRY, PHR, nMag, or pMag.

In the above fusion protein, the partner protein is a protein which can form a heterodimer with the light-induced heterodimerization protein by light irradiation, and the partner protein may be CIB, CIBN, PhyB, PIF6, FKF1, GIGANTEA, CRY, PHR, nMag, or pMag. The partner protein may be CRY or PHR when the light-induced heterodimerization protein is CIB or CIBN; the partner protein may be PIF when the light-induced heterodimerization protein is PhyB; the partner protein may be GIGANTEA when the light-induced heterodimerization protein is FKF1, whereas the partner protein may be CIB or CIBN when the light-induced heterodimerization protein is CRY or PHR; the partner protein may be PhyB when the light-induced heterodimerization protein is PIF; the partner protein may be FKF1 when the light-induced heterodimerization protein is GIGANTEA; the partner protein may be pMag when the light-induced heterodimerization protein is nMag, whereas the partner protein may be nMag when the light-induced heterodimerization protein is pMag. Meanwhile, the PIF may be PIF3 or PIF6.

In the above fusion protein, the light-induced heterodimerization protein or partner protein can form a homodimer by light irradiation. In this case, the light-induced dimerization protein or partner protein that can form a homodimer by light irradiation may be CRY or PHR.

In accordance with another aspect of the present disclosure, there is provided a polynucleotide encoding the fusion protein.

In accordance with another aspect of the present disclosure, there is provided a recombinant vector including the polynucleotide. The recombinant vector may include, in addition to the polynucleotide, a transcription regulatory factor, for example, a promoter, an enhancer, a terminator, etc., for expressing the polynucleotide.

In accordance with another aspect of the present disclosure, there is provided a composition comprising the fusion protein.

The composition may be a pharmaceutical composition used for the treatment of diseases that occur due to the overexpression of an antigen.

In accordance with another aspect of the present disclosure, there is provided a pharmaceutical composition used for the treatment of diseases that occur due to the overexpression of an antigen and containing the recombinant vector as an active ingredient.

In accordance with another aspect of the present disclosure, the provided is a method for activating the antibody analogue, the method including: introducing a first fusion protein comprising an inactive first fragment of an antibody analogue is fused to a stimulus-induced dimerization protein, and a second fusion protein comprising an inactive second fragment of an antibody analogue is fused to a stimulus-induced dimerization partner protein which forms a dimer with the stimulus-induced dimerization protein upon stimulation, wherein the inactive second fragment recovers antigen-binding capacity when bound to the inactive first fragment by dimerizing of the stimulus-induced dimerization protein and the stimulus-induced dimerization partner protein induced by a stimulus to a subject, tissue, or cell; and applying the stimulus to the subject, tissue or cell, wherein the stimulus induces dimerization of the stimulus-induced dimerization protein and the stimulus-induced dimerization partner protein.

In accordance with another aspect of the present disclosure, the provided is a method for activating the antibody analogue, the method including: transducing a subject, tissue or cell with a first polynucleotide encoding a first fusion protein comprising an inactive first fragment of an antibody analogue is fused to a stimulus-induced dimerization protein, and a second polynucleotide encoding a second fusion protein comprising an inactive second fragment of an antibody analogue is fused to a stimulus-induced dimerization partner protein which forms a dimer with the stimulus-induced dimerization protein upon stimulation, wherein the inactive second fragment recovers antigen-binding capacity when bound to the inactive first fragment by dimerizing of the stimulus-induced dimerization protein and the stimulus-induced dimerization partner protein induced by a stimulus; and applying the stimulus to the subject, tissue or cell, wherein the stimulus induces dimerization of the stimulus-induced dimerization protein and the stimulus-induced dimerization partner protein.

In the above method, the antibody analogue may be Fab, F(ab')₂, Fab', $V_HH$, monobody, VLR, Affibody, Affilin, Affimer, Affitin, Alphabody, Anticlin, Avimer, DARpin, Fynomoer, or Kunitz domain peptide.

In the above method, the fusion protein may further include a fluorescent protein.

In particular, the fluorescent protein may be a green fluorescent protein (GFP), a yellow fluorescent protein (YFP), a red fluorescent protein (RFP), an orange fluorescent protein (OFP), a cyan fluorescent protein (CFP), a blue fluorescent protein (BFP), a far-red fluorescent protein, or tetracystein motif. In particular, the green fluorescent protein may be enhanced green fluorescent protein (EGFP), Emerald, Superfolder, GFP, Azami Green, TagGFP, TurboGFP, ZsGreen, or T-Sapphire; the yellow fluorescent protein may be enhanced yellow fluorescent protein (EYFP), Topaz, Venus, mCitrine, Ypet, TagYFP, PhiYFP, ZsYellow1, or mBanana; the red fluorescent protein may be mRuby, mApple, mStrawberry, AsRed2, or mRFP; the orange fluorescent protein may be Kusabira Orange, Kusabira Orange2, mOrange, mOrange2, dTomato, dTomato-Tandem, TagRFP, TagRFP-T, DsRed, DsRed2, DsRed-Express, DsRed-Monomer, or mTangerine; the cyan fluorescent protein may be enhanced cyan fluorescent protein (ECFP), mECFP, mCerulean, CyPet, AmCyan1, Midori-Ishi Cyan, TagCFP, or mTFP1; the blue fluorescent protein may be enhanced blue fluorescent protein (EBFP), EBFP2, Azurite, or mTagBFP; the far-red fluorescent protein may be mPlum, mCherry, dKeima-Tandem, JRed, mRaspberry, HcRed1, HcRed-Tandem, or AQ143; and the tetracysteine motif may be a polypeptide which includes the sequence of Cys-Cys-Xaa-Xaa-Cys-Cys (SEQ ID NO: 1), in which the Xaa may be an amino acid excluding cysteine.

In the above method, the stimulus may be a ligand or light the stimulus-induced dimerization protein is a ligand-induced dimerization protein when the above stimulus is a ligand and a protein which forms a dimer with the ligand-induced dimerization protein is a ligand-induced dimerization partner protein, and the stimulus-induced dimerization protein is a light-induced dimerization protein when the stimulus is light and a protein which forms a dimer with the light-induced dimerization protein is a light-induced dimerization partner protein.

The ligand-induced dimerization protein may be FK506 binding protein (FKBP), Calcineurin A, Cyp-Fas, FKBP-rapamycin-binding protein (FRB), GyrB, GAI (gibberellin insensitive), GID1(gibberellin insensitive dwarf 1), Snap-tag, or Halo-tag.

The ligand-induced dimerization partner protein may be FKBP, Calcineurine, Cyp-Fas, or FRB when the ligand-induced dimerization protein is FKBP; the ligand-induced dimerization partner protein may be FKBP when the ligand-induced dimerization protein is Calcineurin A, Cyp-Fas, or FRB; the ligand-induced dimerization partner protein may be GyrB when the ligand-induced dimerization protein is GyrB; the ligand-induced dimerization partner protein may be GID1 when the ligand-induced dimerization protein is GAI, whereas the ligand-induced dimerization partner protein may be GAI when the ligand-induced dimerization protein is GID1; and the ligand-induced dimerization partner protein may be Halo-tag when the ligand-induced dimerization protein is Snap-tag, whereas the ligand-induced dimerization partner protein may be Snap-tag when the ligand-induced dimerization protein is Halo-tag.

In the above case, the ligand which induces a homodimer between FKBP and FKBP is FK1012; the ligand which induces a heterodimer between FKBP and Calcineurin A is FK506; the ligand which induces a heterodimer between FKBP and Cyp-Fas is FKCsA; the ligand which induces a heterodimer between FKBP and FRB is rapamycin; the ligand which induces a homodimer between GyrB and CyrB is coumermycin; the ligand which induces a heterodimer between GAI and GID1 is gibberellin; and the ligand which induces a heterodimer between Snap-tag and Halo-Tag is HaXS.

In the above case, the light-induced dimerization protein may be a light-induced heterodimerization protein and/or light-induced homodimerization protein. The light-induced heterodimerization protein may be cryptochrome-interacting basic-helix-loop-helix protein (CIB), N-terminal domain of CIB (CIBN), phytochrome (Phy), phytochrome interacting factor (PIF), Flavin-binding, Kelch repeat, F-box 1 (FKF1), GIGANTEA, chryptochrome (CRY), phytolyase homologous region (PHR), nMag, or pMag; and the light-induced homodimerization protein may be CRY or PHR. Conventionally, CRY or PHR is known to form homodimers irrespective of light irradiation, but the present inventors have discovered that CRY or PHR forms homodimers by light irradiation. Therefore, CRY or PHR is a protein which can not only form heterodimers by light irradiation, but also forms homodimer by light irradiation.

In the above case, the light-induced dimerization protein may be a light-induced heterodimerization protein or light-induced homodimerization protein, and the light-induced heterodimerization protein may be CIB, CIBN, PhyB, PIF, FKF1, GIGANTEA, CRY, PHR, nMag, or pMag.

In the above case, the partner protein is a protein which can form a heterodimer with the light-induced heterodimerization protein by light irradiation, and the partner protein may be CIB, CIBN, PhyB, PIF6, FKF1, GIGANTEA, CRY, PHR, nMag, or pMag. The partner protein may be CRY or PHR when the light-induced heterodimerization protein is CIB or CIBN; the partner protein may be PIF when the light-induced heterodimerization protein is PhyB; the partner protein may be GIGANTEA when the light-induced heterodimerization protein is FKF1, whereas the partner protein may be CIB or CIBN when the light-induced heterodimerization protein is CRY or PHR; the partner protein may be PhyB when the light-induced heterodimerization protein is PIF; the partner protein may be FKF1 when the light-induced heterodimerization protein is GIGANTEA; the partner protein may be pMag when the light-induced heterodimerization protein is nMag, whereas the partner protein may be nMag when the light-induced heterodimerization protein is pMag. Meanwhile, the PIF may be PIF3 or PIF6.

In the above case, the light-induced heterodimerization protein or partner protein can form a homodimer by light irradiation. In particular, the light-induced dimerization protein or partner protein that can form a homodimer by light irradiation may be CRY or PHR.

In the above case, the light-induced heterodimerization protein or partner protein can form a homodimer by light irradiation. In particular, the light-induced heterodimerization protein or partner protein that can form a homodimer by light irradiation may be CRY or PHR.

Based on predictions about the tertiary structure of scFv and nanobody ($V_HH$), which are the antibody analogues, the present inventors have designed recombinant antibody analogue fragments (a first fragment and a second fragment) that specifically bind to GFP or GCN4 peptides so as to be cut at the linker or non-CDR loop portion that does not affect the structure of the CDR portion, after which the present inventors have prepared polynucleotides respectively encoding a 1a fusion protein, in which nMag (i.e., a light-induced dimer protein) and a fluorescent protein are linked to the C-terminal of the first fragment among these fragments, and a 2a fusion protein, in which a fluorescent protein and pMag (i.e., the partner protein of the light-induced dimerization protein) are linked to the N-terminal of the second fragment among these fragments. Subsequently, recombinant expression vectors were prepared by cloning these polynucleotides to expression vectors, and co-transfected in HeLa cells to express the fusion proteins. In the case where they were simply expressed, the fusion proteins did not detect any antigens. However, when the cells were irradiated with light having a wavelength of 488 nm capable of inducing the light-induced dimerization, it was confirmed that the antigen present in the nucleus or cytoplasm was accurately detected (see FIGS. 7 to 9).

This demonstrates that the fusion proteins of the present invention can be used to bind to and detect antigens that are targeted upon light irradiation.

Furthermore, in addition to the light-induced dimerization protein, the present inventors designed fusion proteins in which FKBP and FRB, which are capable of forming a dimer by a ligand, are linked to the above-mentioned split antibody analogue fragments, after which the present inventors prepared gene constructs designed for the expression of the fusion proteins, and then co-transfected the gene constructs into HeLa cells. The present inventors experimentally demonstrated that the antigen-binding capacity according to dimerization could be recovered upon treatment of rapamycin, which is a ligand capable of inducing a dimerization between FKBP and FRB (see FIGS. 10 and 11). Accordingly, the fusion proteins of the present invention and the method using the fusion proteins can be used to temporarily and locally detect or inactivate antigens in a cell, and thus, the present invention can be effectively used for studying the functions of a specific protein or for treating diseases by inhibiting specific proteins.

MODES FOR CARRYING OUT THE INVENTION

Hereinafter, the present invention will be described in more detail with reference to Examples and Experimental Examples. However, the present invention is not limited to the embodiments and experimental examples described below, but may be implemented in various other forms, and the following examples and experimental examples are provided to make the disclosure of the invention complete and help those skilled in the art to fully understand the scope of the invention.

Example 1: Preparation of N-Term $V_H$HGFP-nMagH-mCherry Construct and iRFP-pMagH-C-Term $V_H$HGFP Construct The $V_H$HGFP construct was purchased from ChromoTek, and the N-term $V_H$HGFP-nMagH-mCherry construct was prepared by inserting the nucleic acid sequence encoding the N-terminal fragment (N-term $V_H$HGFP, SEQ ID NO: 2) consisting of amino acids at positions 1 to 65 of $V_H$HGFP in the $V_H$HGFP construct, a (GGGGS)$_2$ linker, and the nucleic acid encoding nMagH (SEQ ID NO: 3) into the N-terminal side of mCherry of the pmCherry construct. The nucleic acid sequence encoding nMagH was synthesized based on the disclosure by Kawano et al. (Kawano et al., *Nat. Comm.*, 6: 6256, 2015). Meanwhile, the $V_H$HGFP-mCherry construct was prepared by inserting the polynucleotide encoding the full-length $V_H$HGFP (SEQ ID NO: 4) from the $V_H$HGFP construct into the mCherry construct, and was used as a positive control.

Meanwhile, the present inventors purchased the piRFP construct (Addgene 31857) and linked thereto the nucleic acid encoding a fusion protein, in which pMagH (SEQ ID NO: 5), a (GGGGS)$_2$ linker, and the C-term $V_H$HGFP (SEQ ID NO: 6) consisting of amino acids at positions 66 to 117 of $V_H$HGFP are sequentially linked, and thereby prepared the iRFP-pMagH-C-term $V_H$HGFP construct.

Example 2: Preparation of N-Term scFvGCN4-nMagH-fuRed Construct and iRFP-pMagH-C-Term scFvGCN4 Construct The pHR-scFv-GCN4-sfGFP-GB1-NLS-dWPRE construct was purchased from Addgene. The nucleic acid sequence corresponding to the N-term scFvGCN4 (SEQ ID NO: 7), which consists of amino acids at positions 1 to 196 in the nucleic acid sequence encoding scFV-GCN4 from the pHR-scFv-GCN4-sfGFP-GB1-NLS-dWPRE, was amplified by PCR, and thereby the N-term scFVGCN4-nMagH-fuRed construct was prepared in the same manner as in the preparation of the N-term $V_H$HGFP-nMagH-mCherry construct prepared in Example 1.

Furthermore, the nucleic acid sequence encoding the C-term scFvGCN4 (SEQ ID NO: 8), which consists of amino acids at positions 197 to 247 of scFv-GCN4 from the pHR-scFv-GCN4-sfGFP-GB1-NLS-dWPRE construct used in Example 2, was inserted after PCR amplification instead of the C-term $V_H$HGFP of the iRFP-pMagH-C-term $V_H$HGFP construct prepared in Example 1, and thereby the iRFP-pMagH-C-term scFvGCN4 construct was prepared.

Example 3: Preparation of N-Term $V_H$HGFP-FRB-fuRed-P2A-FKBP-C-Term $V_H$HGFP Construct The nMagH-mCherry was removed from the N-term $V_H$HGFP-nMagH-mCherry construct prepared in Example 1, and a polynucleotide encoding a fusion protein, in which FRB (SEQ ID NO: 9)-fuRed (SEQ ID NO: 10)-P2A (SEQ ID NO: 11)-FKBP (SEQ ID NO: 12), and the C-term $V_H$HGFP(SEQ ID NO: 6) are sequentially linked, was inserted therein, and thereby the N-term $V_H$HGFP-FRB-fuRed-P2A-FKBP-C-term $V_H$HGFP construct was prepared. The polynucleotides were prepared by PCR after preparing overlapping primers to link polynucleotides encoding each of the proteins.

Example 4: Preparation of N-Term VHHActin-FRB-fuRed-P2A-FKBP-C-Term VHHActin Construct The $V_H$HActin construct was purchased from ChromoTek. The nucleic acid sequence encoding the N-terminal fragment (N-term $V_H$HActin, SEQ ID NO: 13), which consists of the amino acids at positions 1 to 64 of $V_H$HActin in the $V_H$HActin construct, and the nucleic acid sequence encoding the C-a terminal fragment (C-term $V_H$HActin, SEQ ID NO: 14), which consists of the amino acids at positions 65 to 122 of $V_H$HActin, were inserted instead of the N-term $V_H$HGFP and the C-term $V_H$HGFP of the N-term $V_H$HGFP-FRB-fuRed-P2A-FKBP-C-term $V_H$HGFP construct prepared in Example 5, respectively, and thereby the N-term $V_H$HActin-FRB-fuRed-P2A-FKBP-C-term $V_H$HActin construct was prepared.

Example 5: Preparation of N-Term V$_H$HActin-nMagH-mCherry Construct and iRFP-pMagH-C-term V$_H$HActin Construct The N-term V$_H$HActin-nMagH-mCherry construct was prepared by inserting a polynucleotide encoding the N-term V$_H$HActin used in Example 4 instead of the N-term V$_H$HGFP of the N-term V$_H$HGFP-nMagH-mCherry construct used in Example 1, and the iRFP-pMagH-C-term V$_H$HActin construct was prepared by inserting a polynucleotide encoding the C-term V$_H$HActin used in Example 4 instead of the C-term V$_H$HGFP of the iRFP-pMagH-C-term V$_H$HGFP construct.

Experimental Example 1: Light-Induced Activation of Split V$_H$H

The present inventors co-transfected the N-term V$_H$HGFP-nMagH-mCherry construct and the iRFP-pMagH-C-term V$_H$HGFP construct prepared in Example 1 into HeLa cells. In particular, since GFP, which is an antigen, is not expressed in HeLa cells, GFP was co-transfected with GFP-H2B construct (Kanda et al., *Curr. Biol.*, 8: 377-385, 1998) or TOMM20-EGFP construct (Komatsu et al., *Nat. Methods*, 7(3): 206-208, 2010) to express the antigen. As a positive control, the V$_H$HGFP-mCherry construct and the GFP-H2B construct or the TOMM20-EGFP construct prepared in Example 1 were used.

Figure 7A:
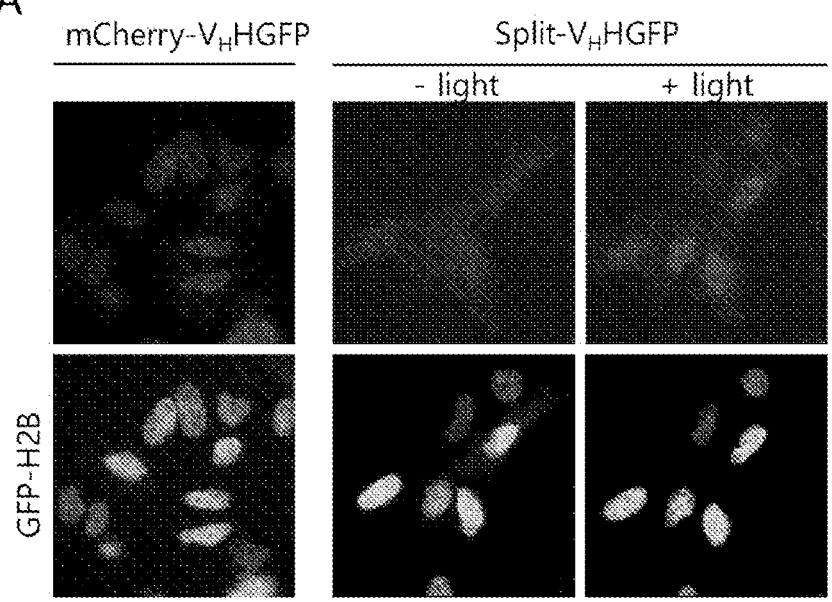
FIGS. 7A and 7B show the results of inducing activation of the split anti-GFP nanobody ($V_HH$) by light irradiation.
Figure 7B:
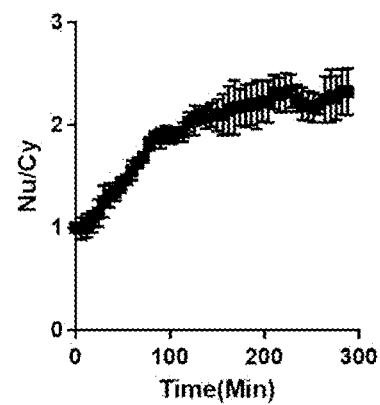

In the case of HeLa cells where GFP-H2B was co-expressed, it was confirmed that upon application of light having a wavelength of 488 nm after the transfection, the V$_H$HGFP gathered toward the nucleus where GFP was expressed and activated (FIG. 7A). FIG. 7B is a graph showing the fluorescence intensity ratio between cytoplasm and nucleus according to time after light irradiation. As shown in FIG. 7B, it was confirmed that the intensity of fluorescence in the nuclei gradually became stronger with the passage of time. This suggests that the split V$_H$HGFP, which was in an inactive state, was converted to the active type V$_H$HGFP due to the interaction between nMag and pMag by light irradiation, and specifically bound to GFP present in nuclei.

Figure 8A:
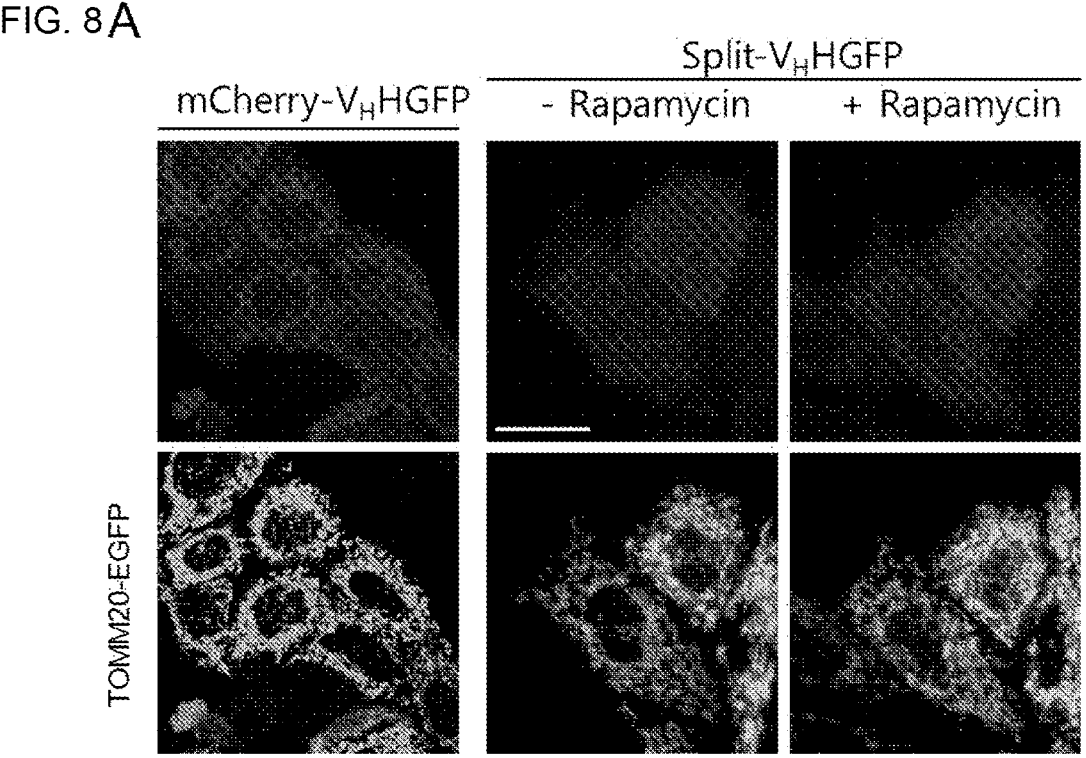
FIGS. 8A and 8B show the results of inducing activation of the split anti-GFP nanobody ($V_HH$) by light irradiation.
Figure 8B:
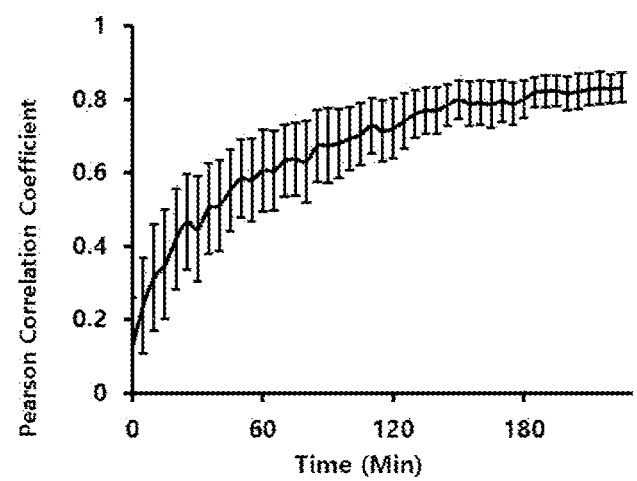

Meanwhile, in the HeLa cells in which TOMM20-EGFP was co-transfected to express GFP, an antigen, in the mitochondria in the cytoplasm, it was confirmed that fluorescence by mCherry, which was localized in the whole cells after light irradiation, moved to the mitochondria (FIG. 8A). FIG. 8B is a graph showing the correlation between fluorescence by GFP and fluorescence by mCherry in the same location in the results of FIG. 8A. As shown in FIG. 8B, it was confirmed that the correlation between green fluorescence and red fluorescence increased with the passage of time. This demonstrates that the split nanobody of the present invention not only forms a dimer by light irradiation but also restores the activity of the nanobody as an antibody analogue.

Furthermore, the present inventors prepared the construct (C-term V$_H$HGFP-pMagH-iRFP), which was designed to position the V$_H$HGFP C-terminal fragment at the N-terminal, and analyzed the construct to examine the effect that the position of the C-terminal fragment of the V$_H$H has in a construct including the C-terminal fragment of V$_H$H. As a result, it was confirmed that although the activation level was slightly lower than that of the iRFP-pMagH-C-term V$_H$HGFP construct prepared in Example 1, the split V$_H$H could likewise be sufficiently activated (data not shown).

Accordingly, the specific position of a split antibody analogue fragment within a fusion protein is not significant.

Experimental Example 2: Light-Induced Activation of Split scFv

In order to examine whether not only the nanobody (V$_H$H) but also ScFv, which is a single-chain antibody analogue fragment, forms a fusion protein between a split and light-induced dimerization protein such that light-induced activation is possible, the present inventors performed an analysis using the N-term scFVGCN4-nMagH-mCherry construct and the iRFP-pMagH-C-term scFvGCN4 construct prepared in Example 2 in which scFv was used instead of V$_H$H.

Specifically, the N-term scFVGCN4-nMagH-mCherry construct and the iRFP-pMagH-C-term scFvGCN4 construct prepared in Example 2 were co-transfected with the mito-GFP-24XGCN4-pep construct, which was designed for the expression of GCN4 (i.e., an antigen) in the cytoplasm, in HeLa cells. The mito-GFP-24XGCN4-pep construct was prepared by substituting the mCherry of the gene construct Mito-mCherry-24XGCN4pep described in a publication by Tanenbaum et al. Tanenbaum et al., *Cell*, 159: 635-646, 2014). In the above construct, Mito represents a mitochondrial target signal sequence, and 24XGCNpep represents a construct in which 24 fragments, which have a size of 22 amino acids and are self-assembled by the coiled-coil method, are linked side by side in the transcription factor GCN4. In particular, the scFvGCN4-fuRed construct was used as a positive control, and the scFvGCN4-fuRed construct was prepared using the pHR-scFv-GCN4-sfGFP-GB1-NLS-dWPRE construct and the pFusionRed-N construct (Evrogen, RUSSIA) used in Example 2.

Figure 9A:
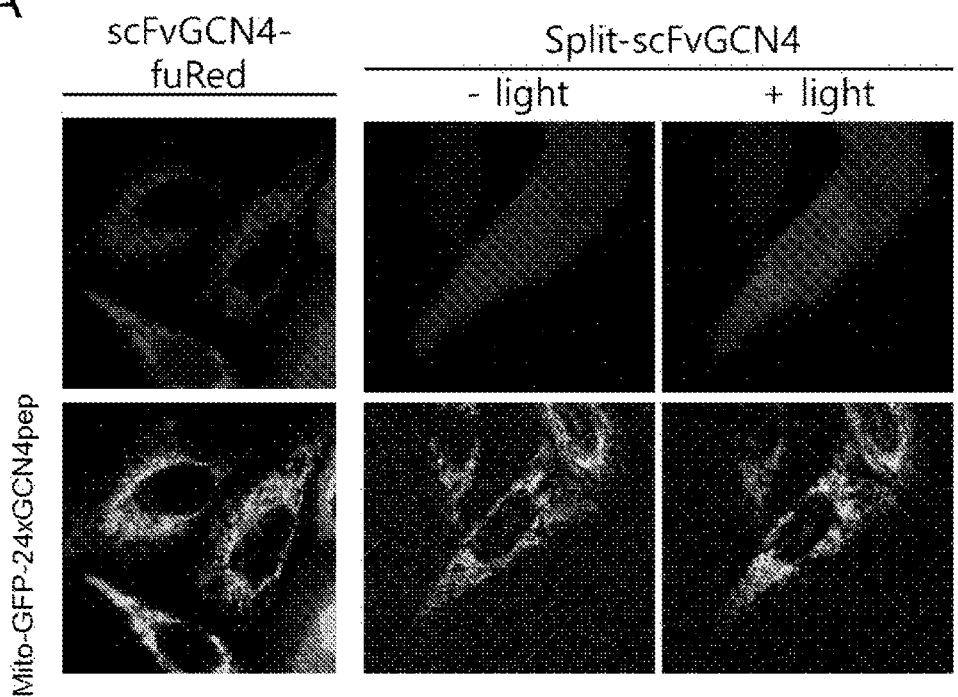
FIGS. 9A and 9B show the results of inducing activation of split anti-GCN4 scFv.
Figure 9B:
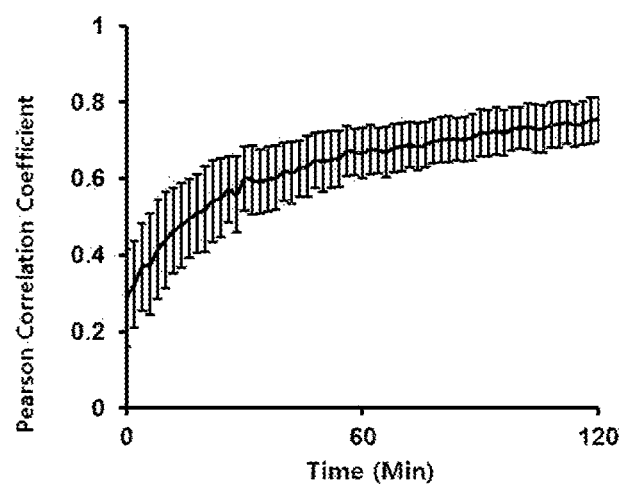

As a result, as shown in FIG. 9A, it was confirmed that the split scFv also recovered its activity as a result of the dimerization of a light-induced dimerization protein by light irradiation, and was specifically bound to an antigen located in mitochondria. FIG. 9B is a graph showing the correlation of red fluorescence to GFP fluorescence in the same position as a ratio. As shown in FIG. 9B, it was confirmed that the intensity of red fluorescence increased at the green fluorescence position with the passage of time after light irradiation. This demonstrates that scFv also transforms from an inactive state to an active state when forming a complex by light irradiation after splitting.

Experimental Example 3: Activation of Split VIM by Ligand

The present inventors examined whether a ligand-induced dimerization protein, which can form a dimer by a ligand in addition to light irradiation, recovers its antigen-binding capacity, in a manner similar to when induced by light, when treated by a ligand after being fused to a split V$_H$H and expressed in a cell.

Specifically, the N-term V$_H$HGFP-FRB-fuRed-P2A-FKBP-C-term V$_H$HGFP construct prepared in Example 3 was co-transfected with the TOMM20-EGFP construct in HeLa cells. The N-term V$_H$HGFP-FRB-fuRed-P2A-FKBP-C-term V$_H$HGFP construct was designed so that the N-terminal fragment of the V$_H$HGFP (a first fragment) and the C-terminal fragment of the V$_H$HGFP (a second fragment), when expressed as a single polypeptide and translated in the ribosome, can be split at the P2A region and expressed in the form of fusion proteins including the two fragments. Nevertheless, it is also possible for the fragments to be prepared as separate constructs as in Examples 1a and 2, and then co-transfected in cells. In fact, the present inventors have confirmed that a similar result was obtained even when the first fragment and the second fragment were expressed as respective constructs (data not shown).

Figure 10A:
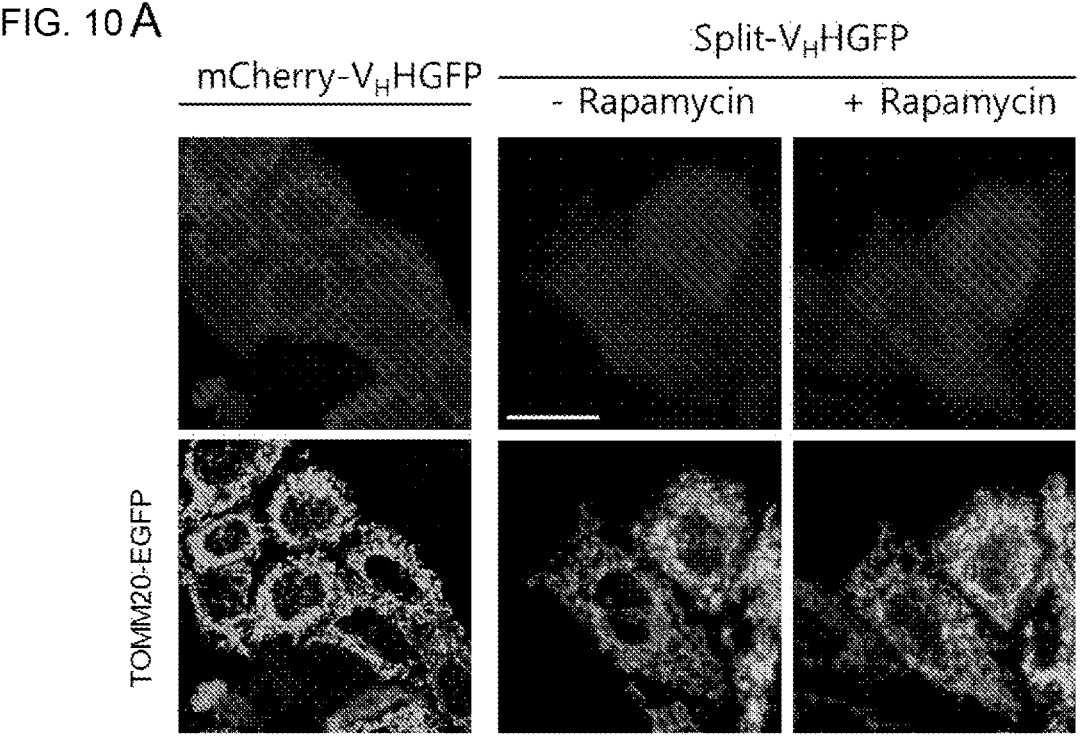
FIGS. 10A and 10B show the results of inducing activation of split anti-GFP nanobody ($V_HH$) by rapamycin treatment.
Figure 10B:
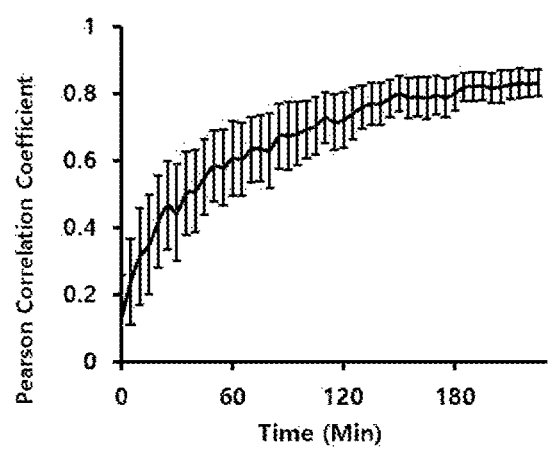

After co-transfection, HeLa cells were treated with 0.1 µM rapamycin, and the distribution of fluorescence and the change in intensity were observed under a fluorescence microscope. As a result, as shown in FIG. 10A, it was confirmed that the intensity of red fluorescence increased in the cytoplasm where EGFP was expressed after rapamycin treatment. As shown in FIG. 10B, it was confirmed that the correlation of red fluorescence to green fluorescence increased at the same position with the passage of time. From these results, it could be seen that the activation of a split antibody analogue is possible using not only light induction, but also a ligand.

Experimental Example 4: Detection of Endogenous Proteins Using Light-Irradiation and Ligands Since GFP is not an endogenous protein present in HeLa cells, in order to confirm whether the system of the present invention can be used to detect proteins that are actually present in cells, the present inventors transfected the N-term $V_H$HActin-FRB-fuRed-P2A-FKBP-C-term $V_H$HActin construct prepared in Example 3 in HeLa cells. Then, the transfected HeLa cells were treated with rapamycin and the shape and intensity of fluorescence in the cells with the passage of time were analyzed.

Figure 11A:
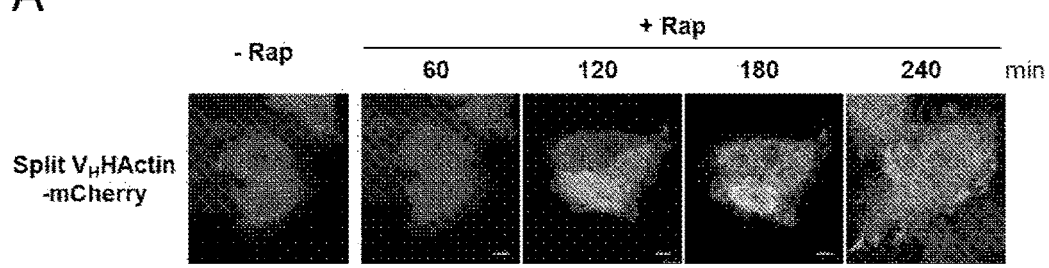
FIGS. 11A and 11B show microscopic images illustrating the results of inducing activation of the split anti-actin nanobody ($V_HH$) using light and rapamycin.

As a result, as shown in FIG. 11A, after the passage of a certain amount of time, red fluorescence appeared in a fibrous form in the cytoplasm where actin was located.

Figure 11B:
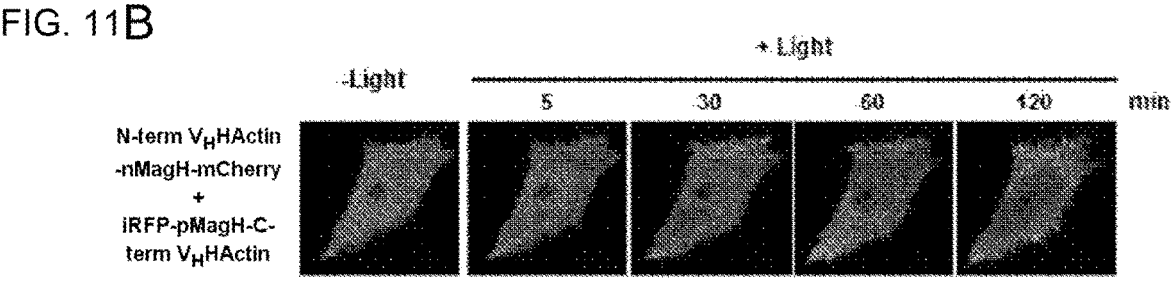

Furthermore, to confirm whether reversible detection of endogenous proteins is possible by dimerization by light induction in addition to the ligand induction, the present inventors co-transfected the N-term $V_H$HActin-nMagH-mCherry construct and the iRFP-pMagH-C-term $V_H$HActin construct prepared in Example 5 in HeLa cells, irradiated the HeLa cells with light having a wavelength of 488 nm, and analyzed the shape and intensity of fluorescence in the cells with the passage of time. As a result, as shown in FIG. 11B, it was confirmed that anti-actin $V_H$H activity was recovered by dimerization of a light-induced dimerization protein by light irradiation, and the anti-actin $V_H$H was specifically distributed at the position of the actin present in the cells. This demonstrates that the system of the present invention can also be used for the detection of endogenous proteins.

The present invention confirms for the first time that the antigen-binding capacity can be recovered by recombination of the above-mentioned inactive fragments when small fragment antibody analogues such as Fab, scFv, and nanobody are split into smaller inactivate fragments, transfected into cells, tissues, or subjects, as a fusion protein partner of each of the stimulus-induced dimerization proteins, and allowed to form a dimer of the dimerization protein by light irradiation or ligand treatment. According to an embodiment of the present invention, efficient utilization in cell biology and biochemistry research, as well as in the development of protein therapeutics and antibody gene therapy methods targeting intracellular heterologous proteins, is possible.

Although the present invention has been described with reference to the Examples and Experimental Examples described above, the Examples and Experimental Examples are merely exemplary, and it will be obvious to those skilled in the art that various alternatives, modifications, and variations can be derived therefrom. Accordingly, the true technical scope of the present invention should only be determined by the technical concept of the appended claims.

INDUSTRIAL APPLICABILITY

The fusion protein according to an embodiment of the present invention can be widely used for real-time confirmation of the functions of specific intracellular proteins or for treatment of specific diseases or the like, by light-induced reversible irradiation or light-induced reversible inhibition of a specific protein carried out by using light to reversibly control the activity of an antibody analogue that can specifically bind to the specific protein in a cell.

SEQUENCING LIST FREE TEXT

SEQ ID NO: 1 is the amino acid sequence of a tetracysteine motif.

SEQ ID NO: 2 is the amino acid sequence of an N-terminal fragment the nanobody ($V_H$HGFP) that specifically binds to GFP.

SEQ ID NO: 3 is the amino acid sequence of nMag.

SEQ ID NO: 4 is the full-length amino acid sequence of $V_H$HGFP.

SEQ ID NO: 5 is the amino acid sequence of pMag.

SEQ ID NO: 6 is the amino acid sequence of the C-terminal fragment of $V_H$HGFP.

SEQ ID NO: 7 is the amino acid sequence of the N-terminal fragment of a single chain variable fragment (scFv) that specifically binds to GCN4.

SEQ ID NO: 8 is the amino acid sequence of the C-terminal fragment of a single chain variable fragment (scFv) that specifically binds to GCN4.

SEQ ID NO: 9 is the amino acid sequence of the FRB protein.

SEQ ID NO: 10 is the amino acid sequence of the Fusion Red protein.

SEQ ID NO: 11 is the amino acid sequence of the KFBP protein.

SEQ ID NO: 12 is the amino acid sequence of P2A.

SEQ ID NO: 13 is the amino acid sequence of the N-terminal fragment of nanobody that specifically binds to Actin.

SEQ ID NO: 14 is the amino acid sequence of the C-terminal fragment of $V_H$HActin.

The invention claimed is:

1. A composition comprising a first polynucleotide encoding a first fusion protein comprising a first antibody fragment fused to a light-induced dimerization protein, and a second polynucleotide encoding a second fusion protein comprising a second antibody fragment fused to a light-induced dimerization partner protein capable of binding of light-induced dimerization protein by light irradiation, wherein binding of light-induced dimerization protein to the light-induced dimerization partner protein induced by light producing a light-activatable antibody,
 wherein when the antibody is scFv, the first antibody fragment is $V_L$, the second antibody fragment is $V_H$,
 wherein when the antibody if Fab, the first antibody fragment is $V_L$-$C_L$, the second antibody fragment is $V_H$-$C_H1$, or
 wherein the antibody is $V_H$, the antibody fragments are cleaved at a non-CDR loop region of $V_H$,
 wherein the light induced dimerization protein is CIB (cryptochrome-interacting basic-helix-loop-helix protein), CIBN (N-terminal region of the CIB, PhyB (phytochrome A), PIF (phytochrome interacting protein), FKF1 (Flavin-binding, Kelch repeat, F-box protein), GIGANTEA, CRY (chryptochrome protein), PHR (N-terminal regioin of CRY), nMag (negative Magnet protein), or pMag (positive Magnet protein);
 wherein the light-inducted idmerization protein is CRY or PHR, the light-induced dimerization partner protein is CIB or CIBN;
 wherein the light-induced dimerization protein is PIF, the light-induced dimerization partner protein in PhyB;
 wherein the light-inducted dimerization protein is GIGANTEA, the light-induced dimerization partner protein in KFK1;
 wherein the light-induced dimerization protein is CIB or CIBN, the light-induced dimerization partner protein is CRY or CIBN;
 wherein the light-induced dimerization protein is PhyB, the light-induced dimerization partner protein in PIF;
 wherein the light-induced dimerization protein is FKF1, the light-induced dimerization partner protein in GIGANTEA;
 wherein the light-induced dimerization protein is pMag, the light-induced dimerization partner protein in nMag; or
 wherein the light-induced dimerization protein is nMag, the light-induced dimerization partner protein in pMag.

2. The composition of claim 1, wherein the first fusion protein and/or the second fusion protein further comprises a fluorescent protein.

3. The composition of claim 2, wherein the fluorescent protein is a green fluorescent protein (GFP), yellow fluorescent protein (YFP), red fluorescent protein (RFP), orange fluorescent protein (OFP), cyan fluorescent protein (CFP), blue fluorescent protein (BFP), far-red fluorescent protein, or tetracystein motif.

* * * * *

SEQUENCE LISTING

<160> NUMBER OF SEQ ID NOS: 16

<210> SEQ ID NO 1
<211> LENGTH: 6
<212> TYPE: PRT
<213> ORGANISM: Artificial Sequence
<220> FEATURE:

```
<223> OTHER INFORMATION: tetracystein motif
<220> FEATURE:
<221> NAME/KEY: VARIANT
<222> LOCATION: (3)..(4)
<223> OTHER INFORMATION: Xaa may be one of any amino acids

<400> SEQUENCE: 1

Cys Cys Xaa Xaa Cys Cys
1               5

<210> SEQ ID NO 2
<211> LENGTH: 65
<212> TYPE: PRT
<213> ORGANISM: Artificial Sequence
<220> FEATURE:
<223> OTHER INFORMATION: N-terminal of VHHGFP

<400> SEQUENCE: 2

Met Asp Gln Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
50                  55                  60

Ser
65

<210> SEQ ID NO 3
<211> LENGTH: 150
<212> TYPE: PRT
<213> ORGANISM: Artificial Sequence
<220> FEATURE:
<223> OTHER INFORMATION: nMagHigh1

<400> SEQUENCE: 3

His Thr Leu Tyr Ala Pro Gly Gly Tyr Asp Ile Met Gly Tyr Leu Asp
1               5                   10                  15

Gln Ile Gly Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Ile Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Ile Ile Pro Val Arg Asp Glu Thr Gly Glu Tyr Arg Tyr Ser Met Gly
130                 135                 140

Phe Gln Cys Glu Thr Glu
145                 150

<210> SEQ ID NO 4
<211> LENGTH: 117
```

<212> TYPE: PRT
<213> ORGANISM: Artificial Sequence
<220> FEATURE:
<223> OTHER INFORMATION: VHHGFP

<400> SEQUENCE: 4

Met Asp Gln Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Cys Asn Val Asn Val Gly Phe Glu Tyr Trp Gly Gln Gly Thr Gln
            100                 105                 110

Val Thr Val Ser Ser
        115

<210> SEQ ID NO 5
<211> LENGTH: 150
<212> TYPE: PRT
<213> ORGANISM: Artificial Sequence
<220> FEATURE:
<223> OTHER INFORMATION: pMagHigh1

<400> SEQUENCE: 5

His Thr Leu Tyr Ala Pro Gly Gly Tyr Asp Ile Met Gly Tyr Leu Arg
1               5                   10                  15

Gln Ile Arg Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150

<210> SEQ ID NO 6
<211> LENGTH: 75
<212> TYPE: PRT
<213> ORGANISM: Artificial Sequence
<220> FEATURE:
<223> OTHER INFORMATION: C-terminal of VHHGFP

```
<400> SEQUENCE: 6

Pro Gly Lys Glu Arg Glu Trp Val Ala Gly Met Ser Ser Ala Gly Asp
1               5                   10                  15

Arg Ser Ser Tyr Glu Asp Ser Val Lys Gly Arg Phe Thr Ile Ser Arg
                20                  25                  30

Asp Asp Ala Arg Asn Thr Val Tyr Leu Gln Met Asn Ser Leu Lys Pro
            35                  40                  45

Glu Asp Thr Ala Val Tyr Tyr Cys Asn Val Asn Val Gly Phe Glu Tyr
    50                  55                  60

Trp Gly Gln Gly Thr Gln Val Thr Val Ser Ser
65                  70                  75

<210> SEQ ID NO 7
<211> LENGTH: 196
<212> TYPE: PRT
<213> ORGANISM: Artificial Sequence
<220> FEATURE:
<223> OTHER INFORMATION: N-terminal of scFvGCN4

<400> SEQUENCE: 7

Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
                20                  25                  30

Val Thr Thr Ser Asn Tyr Ala Ser Trp Val Gln Glu Lys Pro Gly Lys
            35                  40                  45

Leu Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
                100                 105                 110

Lys Arg Gly Gly Gly Gly Ser Gly Gly Gly Ser Gly Gly Gly Gly
        115                 120                 125

Ser Ser Gly Gly Gly Ser Glu Val Lys Leu Leu Glu Ser Gly Gly Gly
        130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
                180                 185                 190

Tyr Asn Ser Ala
        195

<210> SEQ ID NO 8
<211> LENGTH: 51
<212> TYPE: PRT
<213> ORGANISM: Artificial Sequence
<220> FEATURE:
<223> OTHER INFORMATION: C-terminal of scFvGCN4

<400> SEQUENCE: 8

Leu Lys Asp Arg Phe Ile Ile Ser Lys Asp Asn Gly Lys Asn Thr Val
1               5                   10                  15
```

-continued

```
Tyr Leu Gln Met Ser Lys Val Arg Ser Asp Asp Thr Ala Leu Tyr Tyr
             20                  25                  30

Cys Val Thr Gly Leu Phe Asp Tyr Trp Gly Gln Gly Thr Leu Val Thr
         35                  40                  45

Val Ser Ser
    50

<210> SEQ ID NO 9
<211> LENGTH: 93
<212> TYPE: PRT
<213> ORGANISM: Artificial Sequence
<220> FEATURE:
<223> OTHER INFORMATION: FRB

<400> SEQUENCE: 9

Ile Leu Trp His Glu Met Trp His Glu Gly Leu Glu Glu Ala Ser Arg
1               5                  10                  15

Leu Tyr Phe Gly Glu Arg Asn Val Lys Gly Met Phe Glu Val Leu Glu
             20                  25                  30

Pro Leu His Ala Met Met Glu Arg Gly Pro Gln Thr Leu Lys Glu Thr
         35                  40                  45

Ser Phe Asn Gln Ala Tyr Gly Arg Asp Leu Met Glu Ala Gln Glu Trp
     50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                 85                  90

<210> SEQ ID NO 10
<211> LENGTH: 232
<212> TYPE: PRT
<213> ORGANISM: Artificial Sequence
<220> FEATURE:
<223> OTHER INFORMATION: Fusion Red(fuRed)

<400> SEQUENCE: 10

Met Val Ser Glu Leu Ile Lys Glu Asn Met Pro Met Lys Leu Tyr Met
1               5                  10                  15

Glu Gly Thr Val Asn Asn His His Phe Lys Cys Thr Ser Glu Gly Glu
             20                  25                  30

Gly Lys Pro Tyr Glu Gly Thr Gln Thr Met Arg Ile Lys Val Val Glu
         35                  40                  45

Gly Gly Pro Leu Pro Phe Ala Phe Asp Ile Leu Ala Thr Ser Phe Met
     50                  55                  60

Tyr Gly Ser Arg Thr Phe Ile Lys His Pro Pro Gly Ile Pro Asp Phe
65                  70                  75                  80

Phe Lys Gln Ser Phe Pro Glu Gly Phe Thr Trp Glu Arg Val Thr Thr
                 85                  90                  95

Tyr Glu Asp Gly Gly Val Leu Thr Ala Thr Gln Asp Thr Ser Leu Gln
             100                 105                 110

Asp Gly Cys Leu Ile Tyr Asn Val Lys Val Arg Gly Val Asn Phe Pro
         115                 120                 125

Ala Asn Gly Pro Val Met Gln Lys Lys Thr Leu Gly Trp Glu Ala Ser
     130                 135                 140

Thr Glu Thr Met Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                 165                 170                 175
```

```
Thr Thr Tyr Arg Ser Lys Lys Pro Ala Thr Asn Leu Lys Met Pro Gly
            180                 185                 190

Val Tyr Asn Val Asp His Arg Leu Glu Arg Ile Lys Glu Ala Asp Asp
        195                 200                 205

Glu Thr Tyr Val Glu Gln His Glu Val Ala Val Ala Arg Tyr Ser Thr
    210                 215                 220

Gly Gly Ala Gly Asp Gly Gly Lys
225                 230

<210> SEQ ID NO 11
<211> LENGTH: 107
<212> TYPE: PRT
<213> ORGANISM: Artificial Sequence
<220> FEATURE:
<223> OTHER INFORMATION: KFBP

<400> SEQUENCE: 11

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 12
<211> LENGTH: 19
<212> TYPE: PRT
<213> ORGANISM: Artificial Sequence
<220> FEATURE:
<223> OTHER INFORMATION: P2A

<400> SEQUENCE: 12

Ala Thr Asn Phe Ser Leu Leu Lys Gln Ala Gly Asp Val Glu Glu Asn
1               5                   10                  15

Pro Gly Pro

<210> SEQ ID NO 13
<211> LENGTH: 64
<212> TYPE: PRT
<213> ORGANISM: Artificial Sequence
<220> FEATURE:
<223> OTHER INFORMATION: N-terminal of VHHActin

<400> SEQUENCE: 13

Met Ala Gln Val Gln Leu Val Glu Ser Gly Gly Gly Leu Thr Gln Ala
1               5                   10                  15

Gly Gly Ser Leu Arg Leu Ser Cys Ala Thr Ser Gly Leu Ile Phe Ser
            20                  25                  30

Ala Phe Gly Met Gly Trp Phe Arg Gln Ala Pro Gly Lys Glu Arg Glu
        35                  40                  45

Phe Val Gly Gly Ile Asn Trp Arg Gly Ser Thr Asn Tyr Gly Asp Phe
```

<210> SEQ ID NO 14
<211> LENGTH: 58
<212> TYPE: PRT
<213> ORGANISM: Artificial Sequence
<220> FEATURE:
<223> OTHER INFORMATION: C-terminal of VHHActin

<400> SEQUENCE: 14

Val Lys Gly Arg Phe Thr Ile Ser Arg Asp Asn Ala Lys Asn Thr Val
1               5                   10                  15

Tyr Leu Gln Met Asn Asn Leu Lys Pro Glu Asp Thr Ala Val Tyr Tyr
            20                  25                  30

Cys Ala Ala Arg Met Val His Lys Thr Glu Tyr Asp Tyr Trp Gly Glu
        35                  40                  45

Gly Thr Gln Val Thr Val Ser Ser Arg Ser
        50                  55

<210> SEQ ID NO 15
<211> LENGTH: 128
<212> TYPE: PRT
<213> ORGANISM: Artificial Sequence
<220> FEATURE:
<223> OTHER INFORMATION: vhhLamin

<400> SEQUENCE: 15

Met Ala Gln Val Gln Leu Gln Glu Ser Gly Gly Gly Leu Val Gln Ala
1               5                   10                  15

Gly Gly Ser Leu Thr Leu Ser Cys Thr Tyr Ser Gly Leu Thr Phe Asp
            20                  25                  30

Asp Tyr Asn Met Gly Trp Phe Arg Gln Gly Pro Gly Lys Glu Arg Glu
        35                  40                  45

Arg Val Ser Ala Ile Ser Phe Arg Gly Ile Thr Tyr Tyr Val Asp Ser
        50                  55                  60

Val Lys Gly Arg Phe Thr Ile Ser Arg Asp Asn Ala Lys Lys Thr Leu
65                  70                  75                  80

Tyr Leu Gln Met Asn Gly Leu Thr Pro Asp Asp Thr Ala Thr Tyr Tyr
            85                  90                  95

Cys Ala Gly Ser Arg Phe Leu Ser Pro Phe Val Arg Asp Gly Asp Thr
            100                 105                 110

Lys Leu Ile Asn Asp Trp Gly Gln Gly Thr Gln Val Thr Val Ser Ser
        115                 120                 125

<210> SEQ ID NO 16
<211> LENGTH: 122
<212> TYPE: PRT
<213> ORGANISM: Artificial Sequence
<220> FEATURE:
<223> OTHER INFORMATION: vhhActin

<400> SEQUENCE: 16

Met Ala Gln Val Gln Leu Val Glu Ser Gly Gly Gly Leu Thr Gln Ala
1               5                   10                  15

Gly Gly Ser Leu Arg Leu Ser Cys Ala Thr Ser Gly Leu Ile Phe Ser
            20                  25                  30

Ala Phe Gly Met Gly Trp Phe Arg Gln Ala Pro Gly Lys Glu Arg Glu
        35                  40                  45

Phe Val Gly Gly Ile Asn Trp Arg Gly Ser Thr Asn Tyr Gly Asp Phe
        50                  55                  60

```
Val Lys Gly Arg Phe Thr Ile Ser Arg Asp Asn Ala Lys Asn Thr Val
65                  70                  75                  80

Tyr Leu Gln Met Asn Asn Leu Lys Pro Glu Asp Thr Ala Val Tyr Tyr
                85                  90                  95

Cys Ala Ala Arg Met Val His Lys Thr Glu Tyr Asp Tyr Trp Gly Glu
            100                 105                 110

Gly Thr Gln Val Thr Val Ser Ser Arg Ser
        115                 120
```